(12) United States Patent
Yoon et al.

(10) Patent No.: US 10,494,343 B2
(45) Date of Patent: Dec. 3, 2019

(54) ORGANIC COMPOUND, NEAR-INFRARED FLUORESCENT CONSTANT MEDIUM CONTAINING SAME, AND METHOD FOR NANO-GRANULATING CONSTANT MEDIUM

(71) Applicants: COLLEGE OF MEDICINE POCHON CHA UNIV. INDUSTRY—ACADEMIC COOPERATION FOUNDATION, Haeryong-ro, Pocheon-si, Gyeonggi-do (KR); CHAMEDITECH CO., LTD, Yuseong-gu, Daejeon (KR)

(72) Inventors: Tae Jong Yoon, Suwon-si (KR); Kwang Hoe Chung, Gyeonggi-do (KR); Jeongbeob Seo, Gyeonggi-do (KR); Sin Wook Kang, Gyeonggi-do (KR); Kwang Hyuong Lee, Seoul (KR); Yong Su Kwon, Gyeonggi-do (KR); Hye Sun Jeon, Gyeonggi-du (KR); Chae Woon Lee, Seoul (KR); Jin Sung Kim, Gyeonggi-do (KR)

(73) Assignees: COLLEGE OF MEDICINE POCHON CHA UNIV. INDUSTRY-ACADEMIC COOPERATION FOUNDATION, Gyeonggi-Do (KR); CHAMEDITECH CO., LTD., Daejeon (KR)

( * ) Notice: Subject to any disclaimer, the term of this patent is extended or adjusted under 35 U.S.C. 154(b) by 0 days.

(21) Appl. No.: 15/542,454

(22) PCT Filed: Jan. 11, 2016

(86) PCT No.: PCT/KR2016/000236
§ 371 (c)(1),
(2) Date: Jul. 10, 2017

(87) PCT Pub. No.: WO2016/111602
PCT Pub. Date: Jul. 14, 2016

(65) Prior Publication Data
US 2018/0327357 A1    Nov. 15, 2018

(30) Foreign Application Priority Data
Jan. 9, 2015  (KR) .......... 10-2015-0003415

(51) Int. Cl.
| A61K 49/00 | (2006.01) |
| C07D 209/60 | (2006.01) |
| B82Y 15/00 | (2011.01) |
| C09B 23/01 | (2006.01) |
| C09B 23/08 | (2006.01) |

(52) U.S. Cl.
CPC ........ *C07D 209/60* (2013.01); *A61K 49/0032* (2013.01); *A61K 49/0052* (2013.01); *A61K 49/0065* (2013.01); *A61K 49/0093* (2013.01); *B82Y 15/00* (2013.01); *C09B 23/0016* (2013.01); *C09B 23/0033* (2013.01); *C09B 23/0066* (2013.01); *C09B 23/086* (2013.01)

(58) Field of Classification Search
CPC .............................. A61K 49/00; C07D 231/06
See application file for complete search history.

(56) References Cited

U.S. PATENT DOCUMENTS

| 5,576,443 A * | 11/1996 | Fabricius ............ C09B 23/0066 544/298 |
| 6,165,671 A | 12/2000 | Weidner et al. |
| 7,488,468 B1 * | 2/2009 | Miwa ................. A61K 49/0032 252/301.22 |
| 2004/0144277 A1 | 7/2004 | Collins et al. |

FOREIGN PATENT DOCUMENTS

| KR | 10-2011-0042152 A | 4/2011 |
| WO | 00-16810 A1 | 3/2000 |

OTHER PUBLICATIONS

International Search Report dated Aug. 24, 2016 in connection with PCT/KR2016/000236.

\* cited by examiner

*Primary Examiner* — Michael G. Hartley
*Assistant Examiner* — Jagadishwar R Samala
(74) *Attorney, Agent, or Firm* — Yakov Sidorin; Angeline Rose Babel; Quarles & Brady LLP

(57) ABSTRACT

The present invention relates to a novel organic compound, a near-infrared fluorescent constant medium containing the same, and a method for nano-granulating the constant medium.

10 Claims, 12 Drawing Sheets

FIG. 4
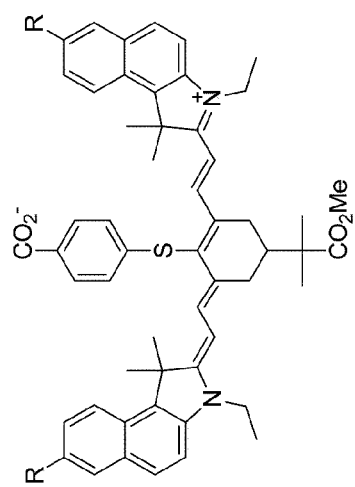
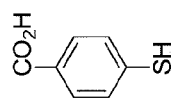
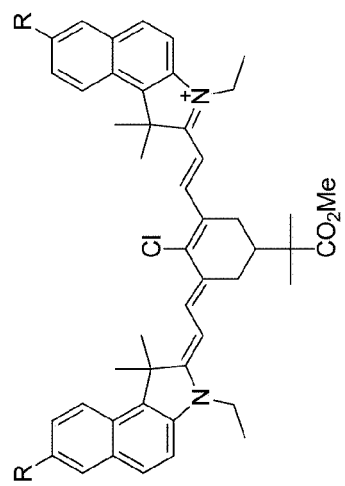

ORGANIC COMPOUND, NEAR-INFRARED FLUORESCENT CONTRAST MEDIUM CONTAINING SAME, AND METHOD FOR NANO-GRANULATING CONSTANT MEDIUM

CROSS-REFERENCE TO RELATED APPLICATIONS

This application represents the national stage entry of PCT International Application No. PCT/KR2016/000236 filed on Jan. 11, 2016, which claims the benefit of Korean Patent Application No. 10-2015-0003415 filed on Jan. 9, 2015. The disclosure of each of these patent applications is incorporated herein by reference for all purposes.

TECHNICAL FIELD

The present invention relates to a novel organic compound, a near-infrared fluorescent contrast medium containing the same, and a method for nano-granulating a contrast medium.

RELATED ART

It is important to detect morphological and functional changes caused by an in vivo disease at an early stage of the disease in the treatment of the disease. Especially in the treatment of cancer, the size and location of a tumor is a crucial determinant of an effective treatment regime. The methods known for this purpose include biopsies by perforation or the like, and imaging diagnostic methods, such as X-ray imaging, MRI, and ultrasound imaging. Biopsies are effective in the final diagnosis, but at the same time, biopsies put a heavy burden on a test subject and are not suitable for tracking the change of a lesion over time. X-ray imaging and MRI inevitably expose a test subject to radiation and electromagnetic waves. Moreover, as mentioned above, conventional imaging diagnostic methods require complex manipulations and take long time for measurement and diagnosis. Moreover, most of the equipments used for the purposes have difficulty in applying these methods during operation.

Fluorescence imaging is one of the imaging methods (Lipspn R. L. et al., J. Natl. Cancer Inst., 26, 1-11 (1961)). In this method, a material that emits fluorescence when exposed to an excitation light having a specific wavelength is used as a contrast medium. Therefore, the body is exposed to an excitation light outside the body, and the fluorescence emitted from a fluorescent contrast medium in the body is detected.

The fluorescent contrast medium may be, for example, a porphyrin compound, such as hematoporphyrin, accumulated in a tumor, and is used in photodynamic therapy (PDT). Other examples are photofrin and benzoporphyrin (see Lipspn R. L. et al., supra, Meng T. S. et al., SPIE, 1641, 90-98 (1992), WO 84/04665, and the like). The compounds are required for PDT, and thus the compounds are originally used for PDT and retain phototoxicity. Ultimately, these compounds are not preferable diagnostic agents.

Meanwhile, retinal circulation microangiography using known fluorescent dyes, such as fluorescein, fluorescamine, and riboflavin has been known (U.S. Pat. No. 4,945,239). The fluorescent dyes emit fluorescence in a visible light region of 400-600 nm. In this region, the light transmission through biological tissues is very low, and consequently, the detection of a lesion in a deeper part of a body is almost impossible.

In addition, the use of cyanine compounds as fluorescent contrast media includes indocyanine green (hereinafter, abbreviated as "ICG"), which is used to determine liver functions and cardiac impulses, and these facts are disclosed in the literature (Haglund M. M. et al., Neurosurgery, 35, 930 (1994); and Li, X. et al., SPIE, 2389, 789-797 (1995)). Cyanine compounds exhibit absorbance in a near-infrared light region (700-1300 nm).

Near-infrared light exhibits high transmission through biological tissues, and can pass through skull bone tissue with a size of about 10 mm. For this reason, near-infrared light has gradually received attention in the field of clinical medicine.

For example, optical CT technology using optical transmission of a medium, which is new technology, has constantly received attention in the clinical field. The reason is that near-infrared light can pass through biological bodies and can be used to monitor the concentration and circulation of oxygen in the body.

Cyanine compounds emit fluorescence in the near-infrared region. The fluorescence in this range can pass through biological tissues and thus has potential as a fluorescent contrast medium. Various cyanine compounds have been recently developed, and attempts have been made as fluorescent contrast media (WO 1996/17628).

However, there exists no agent that has sufficient solubility in water, is safe in biological bodies, and has the ability to distinguish diseased tissues from normal tissues (select target sites through imaging).

DETAILED DESCRIPTION

Technical Problem

An aspect of the present invention is to provide a novel compound having an absorption wavelength and an emission wavelength in a near-infrared light region.

Another aspect of the present invention is to provide a contrast medium, which has sufficient solubility in water, is safe in biological bodies, and has the ability to image and select a target site.

Technical Solution

The present invention relates to a compound represented by Chemical Formula 1 or a salt thereof:

[Chemical Formula 1]

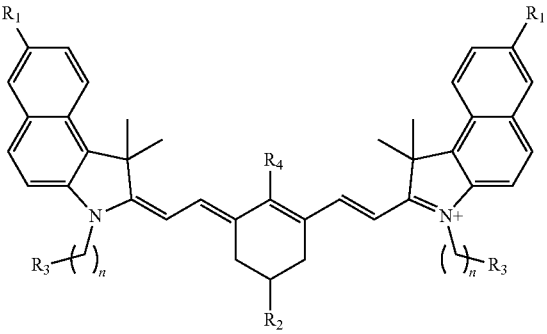

wherein,
$R_1$'s are each independently selected from —Br, —$SO_3H$, or —OMe;
$R_2$ is $R_5$,

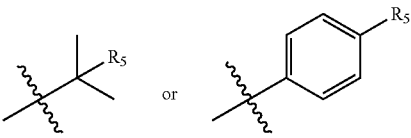

(here, $R_5$ is —H, —$CO_2H$, $C_1$-$C_3$ alkyl, or $C_1$-$C_4$ alkylester);

$R_3$'s are each independently selected from —$SO_3H$, —$CO_2H$, or -Me;

$R_4$ is —Cl or —S—$R_5$ (wherein, $R_6$ is

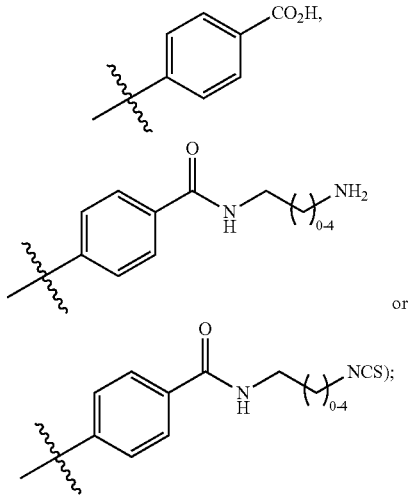

or and n is 0 to 4.

Furthermore, the present invention relates to a near-infrared fluorescent contrast medium containing, as an active ingredient, the compound of Chemical Formula 1 or a pharmaceutically acceptable salt thereof.

Advantageous Effects

The novel compounds according to the present invention have an advantage of having longer absorption and emission wavelengths than existing indocyanine green (ICG) compounds. Therefore, the contrast medium containing the novel compound according to the present invention has excellent transmission when passing through biological tissues, and has an excellent image depth when used as a contrast medium, thereby allowing the detection of lesions in a deeper part of a biological body.

BRIEF DESCRIPTION OF THE DRAWINGS

FIGS. 1 to 6 illustrate synthesis schemes of a compound represented by Chemical Formula 1 according to an embodiment of the present invention.

MODE FOR CARRYING OUT THE INVENTION

Figure 1:
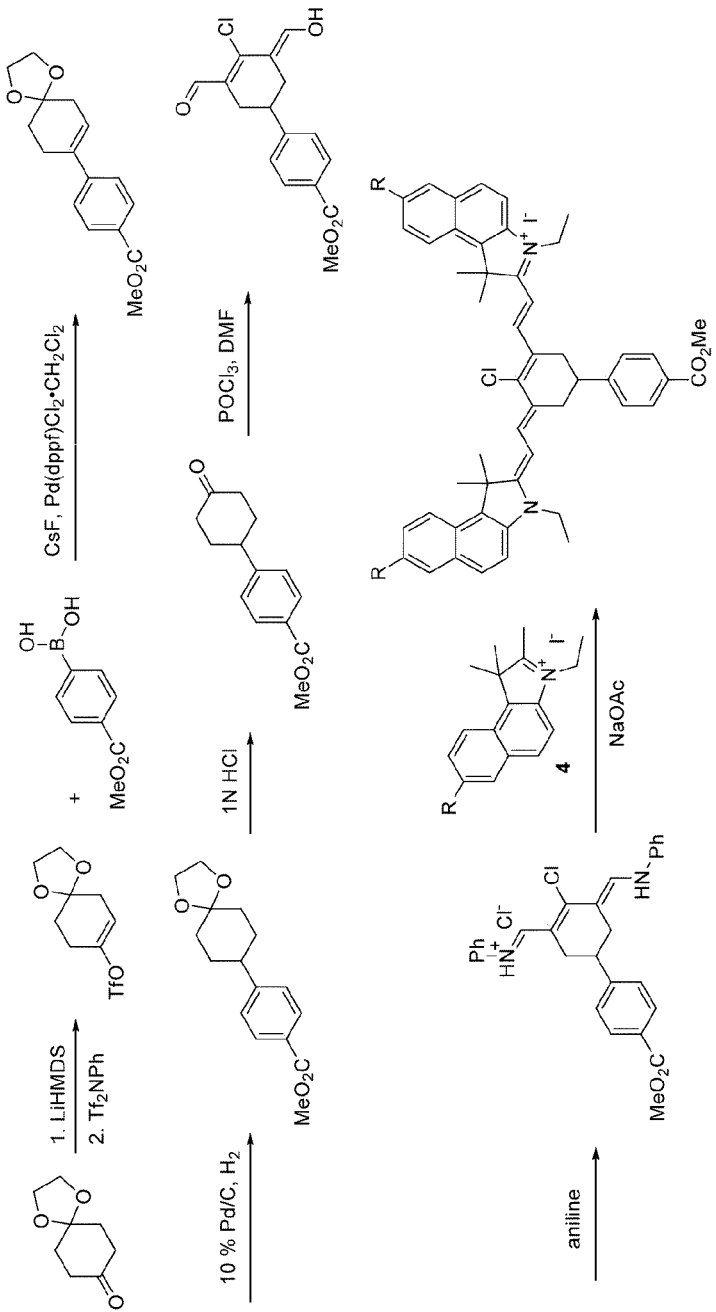
Figure 2:
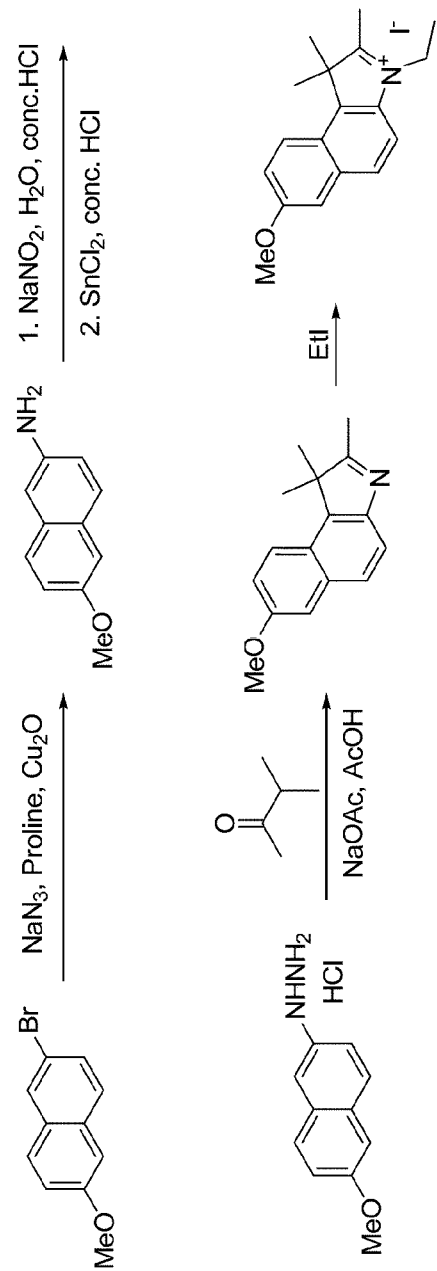
Figure 3:
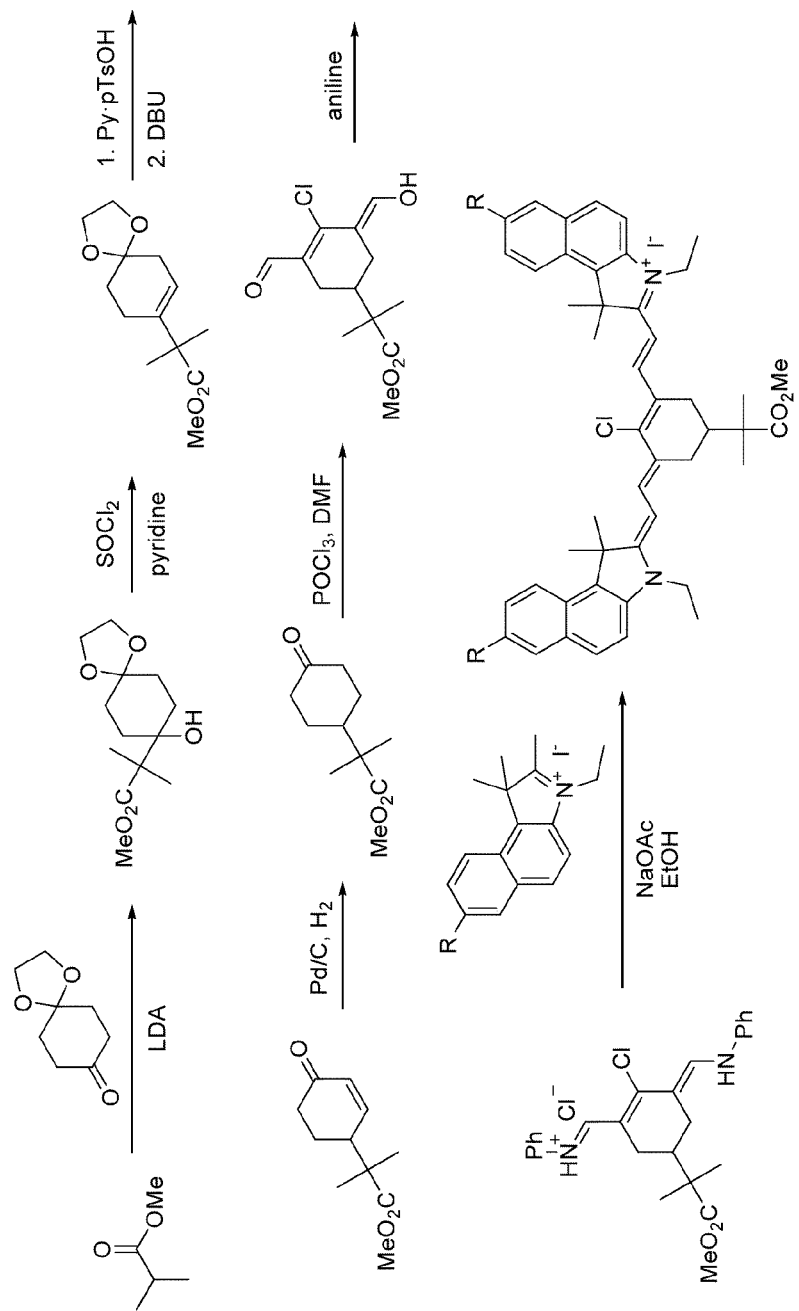
Figure 5:
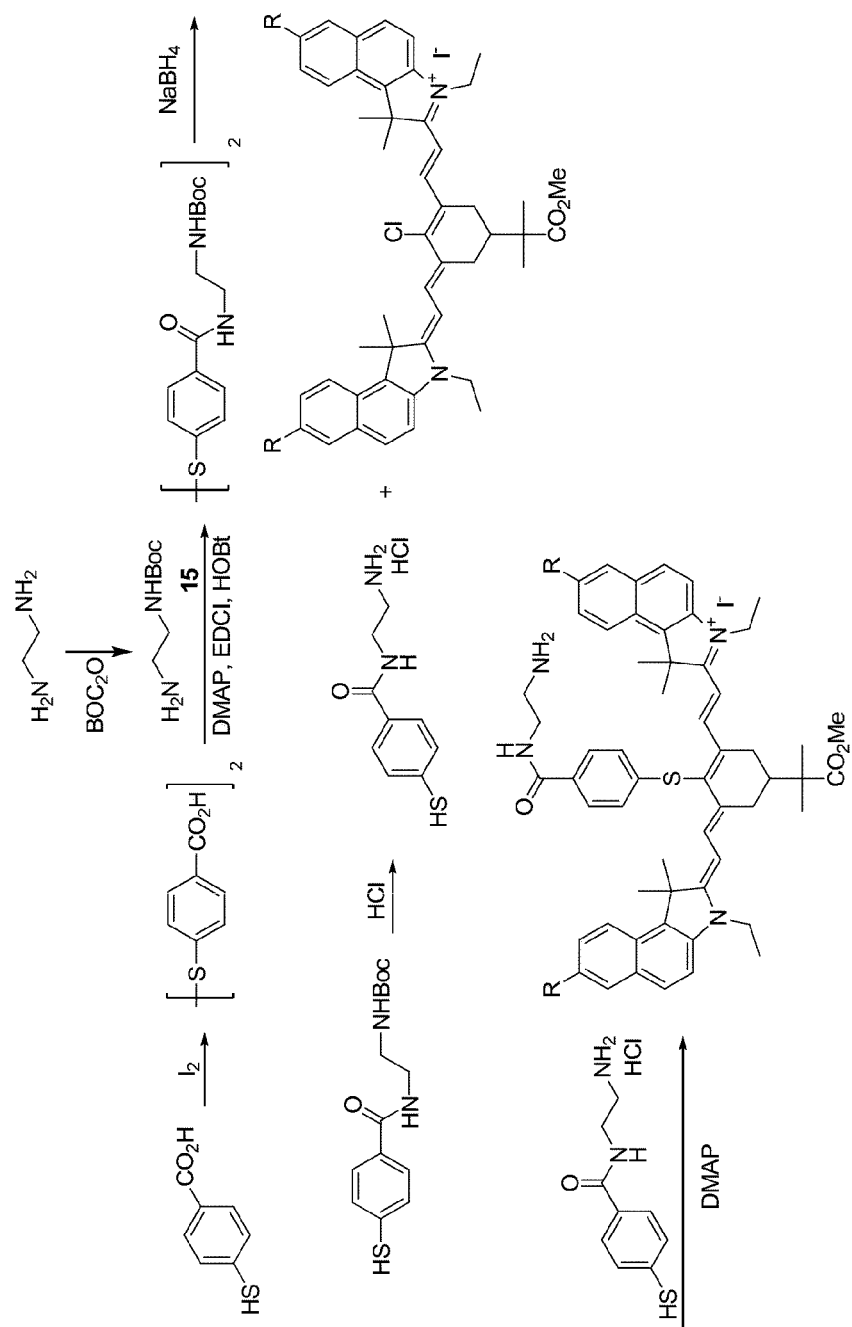
Figure 6:
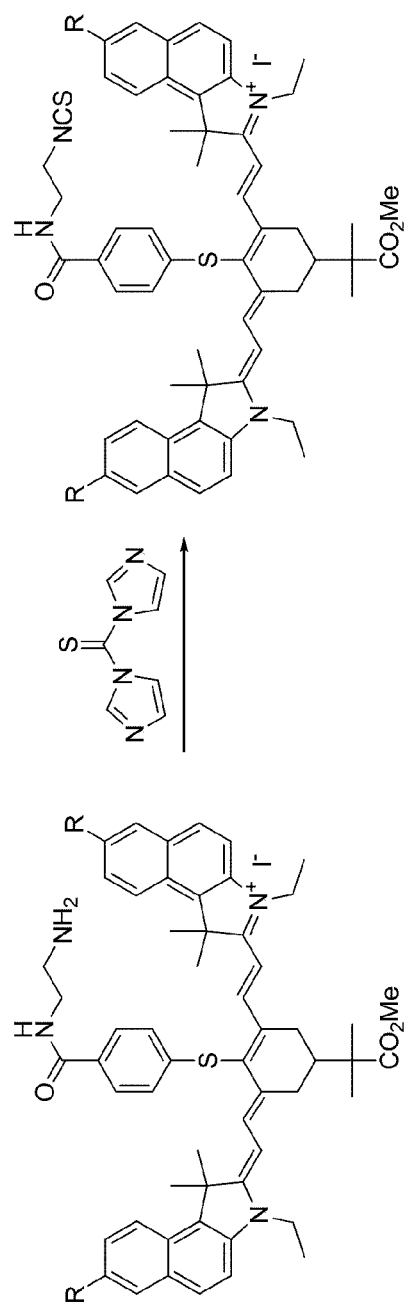

Hereinafter, the present invention will be described in detail. However, the present invention may be realized in various different forms, and therefore is not limited to the embodiments to be described herein.

The present invention relates to a compound represented by Chemical Formula 1 or a salt thereof:

[Chemical Formula 1]

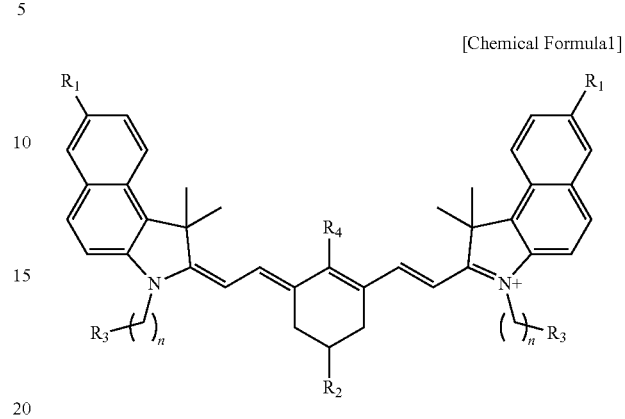

wherein, $R_1$'s are each independently selected from —Br, —$SO_3H$, or —OMe;

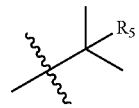

(here, $R_5$ is —H, —$CO_2H$, $C_1$-$C_3$ alkyl, or $C_1$-$C_4$ alkylester);

$R_3$'s are each independently selected from —$SO_3H$, —$CO_2H$, or -Me;

$R_4$ is —Cl or —S—$R_5$ (wherein, $R_6$ is

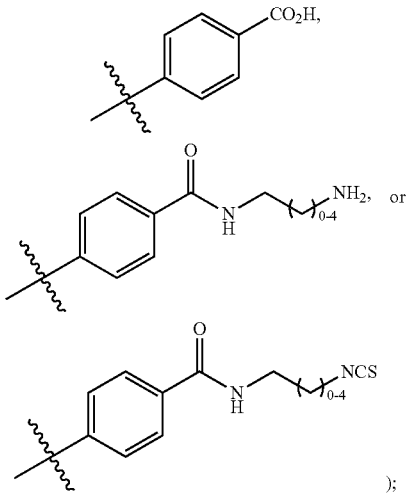

and n is 0 to 4.

When $R_4$ is —S—$R_6$, $R_2$ may be

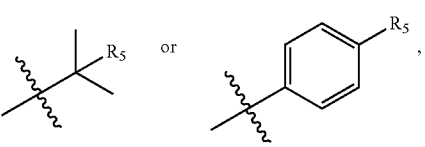

and $R_3$ may be -Me.

When R₄ is —Cl, R₁ may be —OMe, and R₂ may be

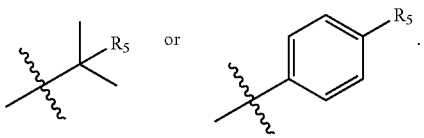

Preferably, Chemical Formula 1 may be selected from the group consisting of 2-((E)-2-((E)-2-chloro-3-((E)-2-(3-ethyl-1,1-dimethyl-7-sulfo-1H-benzo[e]indo-1-2(3H)-ylidene)ethylidene)-5-(4-(methoxycarbonyl)phenyl)cyclohex-1-enyl)vinyl)-3-ethyl-1,1-dimethyl-1H-benzo[e]indolium-7-sulfonate;

7-bromo-2-((E)-2-((E)-3-((E)-2-(7-bromo-3-ethyl-1,1-dimethyl-1H-benzo[e]indol-2(3H)-ylidene)ethylidene)-2-chloro-5-(4-(methoxycarbonyl)phenyl)cyclohex-1-enyl)vinyl)-3-ethyl-1,1-dimethyl-1H-benzo[e]indolium iodide;

2-((E)-2-((E)-2-chloro-3-((E)-2-(3-ethyl-7-methoxy-1,1-dimethyl-1H-benzo[e]indol-2(3H)-ylidene)ethylidene)-5-(4-(methoxycarbonyl)phenyl)cyclohex-1-enyl)vinyl)-3-ethyl-7-methoxy-1,1-dimethyl-1H-benzo[e]indolium iodide;

2-((E)-2-((E)-2-chloro-3-((E)-2-(3-ethyl-1,1-dimethyl-7-sulfo-1H-benzo[e]indol-2(3H)-ylidene)ethylidene)-5-(1-methoxy-2-methyl-1-oxopropan-2-yl)cyclohex-1-enyl)vinyl)-3-ethyl-1,1-dimethyl-1H-benzo[e]indolium-7-sulfonate;

7-bromo-2-((E)-2-((E)-3-((E)-2-(7-bromo-3-ethyl-1,1-dimethyl-1H-benzo[e]indol-2(3H)-ylidene)ethylidene)-2-chloro-5-(1-methoxy-2-methyl-1-oxopropan-2-yl)cyclohex-1-enyl)vinyl)-3-ethyl-1,1-dimethyl-1H-benzo[e]indolium iodide;

2-((E)-2-((E)-2-chloro-3-((E)-2-(3-ethyl-7-methoxy-1,1-dimethyl-1H-benzo[e]indol-2(3H)-ylidene)ethylidene)-5-(1-methoxy-2-methyl-1-oxopropan-2-yl)cyclohex-1-enyl)vinyl)-3-ethyl-7-methoxy-1,1-dimethyl-1H-benzo [e]indolium iodide;

2-((E)-2-((E)-2-(4-carboxyphenylthio)-3-((E)-2-(3-ethyl-1,1-dimethyl-7-sulfo-1H-benzo[e]indol-2(3H)-ylidene)ethylidene)-5-(1-methoxy-2-methyl-1-oxopropan-2-yl)cyclohex-1-enyl)vinyl)-3-ethyl-1,1-dimethyl-1H-benzo[e]indolium-7-sulfonate;

4-((E)-6-((E)-2-(3-ethyl-7-methoxy-1,1-dimethyl-1H-benzo[e]indol-2(3H)-ylidene)ethylidene)-2-((E)-2-(3-ethyl-7-methoxy-1,1-dimethyl-1H-benzo[e]indolium-2-yl) vinyl)-4-(1-methoxy-2-methyl-1-oxopropan-2-yl)cyclohex-1-enylthio)benzoate;

2-((E)-2-((E)-2-(4-(2-aminoethylcarbamoyl)phenylthio)-3-((E)-2-(3-ethyl-7-methoxy-1,1-dimethyl-1H-benzo[e]indol-2(3H)-ylidene)ethylidene)-5-(1-methoxy-2-methyl-1-oxopropan-2-yl)cyclohex-1-enyl)vinyl)-3-ethyl-7-methoxy-1,1-dimethyl-1H-benzo[e]indolium iodide;

3-ethyl-2-((E)-2-((E)-3-((E)-2-(3-ethyl-7-methoxy-1,1-dimethyl-1H-benzo[e]indol-2(3H)-ylidene)ethylidene)-2-(4-(2-isothiocyantoethylcarbamoyl)phenylthio)-5-(1-methoxy-2-methyl-1-oxopropan-2-yl)cyclohex-1-enyl)vinyl)-7-methoxy-1,1-dimethyl-1H-benzo[e]indolium iodide;

2-((E)-2-((E)-2-(4-(2-aminoethylcarbamoyl)phenylthio)-3-((E)-2-(3-ethyl-7-methoxy-1,1-dimethyl-1H-benzo[e]indol-2(3H)-ylidene)ethylidene)cyclohex-1-enyl)vinyl)-3-ethyl-7-methoxy-1,1-dimethyl-1H-benzo[e]indolium iodide;

3-ethyl-2-((E)-2-((E)-3-((E)-2-(3-ethyl-7-methoxy-1,1-dimethyl-1H-benzo[e]indol-2(3H)-ylidene)ethylidene)-2-(4-(2-isothiocyantoethylcarbamoyl)phenylthio)-5-(1-methoxy-2-methyl-1-oxopropan-2-yl)cyclohex-1-enyl)vinyl)-7-methoxy-1,1-dimethyl-1H-benzo[e]indolium iodide;

2-((E)-2-((E)-2-(4-(2-aminoethylcarbamoyl)phenylthio)-3-((E)-2-(3-ethyl-7-methoxy-1,1-dimethyl-1H-benzo[e]indol-2(3H)-ylidene)ethylidene)cyclohex-1-enyl)vinyl)-3-ethyl-7-methoxy-1,1-dimethyl-1H-benzo[e]indolium iodide; and 2-((E)-2-((E)-2-(4-(2-aminoethylcarbamoyl)phenylthio)-5-tert-butyl-3-((E)-2-(3-ethyl-7-methoxy-1,1-dimethyl-1H-benzo[e]indol-2(3H)-ylidene)ethylidene)cyclohex-1-enyl)vinyl)-3-ethyl-7-methoxy-1,1-dimethyl-1H-benzo[e]indolium iodide.

TABLE 1

| Compound | Structural Formula | Name | Absorption/Emission wavelength (Solvent) |
|---|---|---|---|
| Compound A (Example 1) | | 2-((E)-2-((E)-2-chloro-3-((E)-2-(3-ethyl-1,1-dimethyl-7-sulfo-1H-benzo[e]indo-l-2(3H)-ylidene)ethylidene)-5-(4-(methoxycarbony))phenyl)cyclohex-1-enyl)vinyl)-3-ethyl-1,1-dimethyl)-1H-benzo[e]indolium-7-sulfonate | 833 nm/ 865 nm (DMSO) |

TABLE 1-continued

| Compound | Structural Formula | Name | Absorption/Emission wavelength (Solvent) |
|---|---|---|---|
| Compound B (Example 2) | | 7-bromo-2-((E)-2-((E)-3-((E)-2-(7-bromo-3-ethy)-1,1-dimethyl-1H-benzo[e]indol-2(3H)-ylidene)ethylidene)-2-chloro-5-(4-(methoxycarbonyl)pheny)cyclohex-1-enyl)vinyl)-3-ethyl-1,1-dimethyl-1H-benzo[e]indolium iodide | 831 nm/ 863 nm (DMSO) |
| Compond C (Example 3) | | 2-((E)-2-((E)-2-chloro-3-((E)-2-(3-ethyl-7-methoxy-1,1-dimethyl-1H-benzo[e]indol-2(3H)-ylidene)ethylidene)-5-(4-(methoxycarbonyl)phenyl)cyclohex-1-enyl)vinyl)-3-ethyl-7-methoxy-1,1-dimethyl-1H-benzo[e]indolium iodide | 843 nm/ 876 nm (DMSO) |
| Compound D (Example 4) | | 2-((E)-2-((E)-2-chloro-3-((E)-2-(3-ethyl-1,1-dimethyl-7-sulfo-1H-benzo[e]indol-2(3H)-ylidene)ethylidene)-5-(1-methoxy-2-methyl-1-oxopropan-2-yl)cyclohex-1-enyl)vinyl)-3-ethyl-1,1-dimethyl-1H-benzo[e]indolium-7-sulfonate | 833 nm/ 861 nm (DMSO) |

TABLE 1-continued

| Compound | Structural Formula | Name | Absorption/Emission wavelength (Solvent) |
|---|---|---|---|
| Compound E (Example 5) | | 7-bromo-2-((E)-2-((E)-3-((E)-2-(7-bromo-3-ethyl-1,1-dimethyl-1H-benzo[e]indol-2(3H)-ylidene)ethylidene)-2-chloro-5-(1-methoxy-2-methyl-1-oxopropan-2-yl)cyclohex-1-enyl)vinyl)-3-ethyl-1,1-dimethyl-1H-benzo[e]indolium iodide | 833 nm/ 865 nm (DMSO) |
| Compound F (Example 6) | | 2-((E)-2-((E)-2-chloro-3-((E)-2-(3-ethyl-7-methoxy-1,1-dimethyl-1H-benzo[e]indol-2(3H)-ylidene)ethylidene)-5-(1-methoxy-2-methyl-1-oxopropan-2-yl)cyclohex-1-enyl)vinyl)-3-ethyl-7-methoxy-1,1-dimethyl-1H-benzo[e]indolium iodide | 843 nm/ 881 nm (DMSO) |
| Compound G (Example 7) | | 2-((E)-2-((E)-2-(4-carboxyphenylthio)-3-((E)-2-(3-ethyl-1,1-dimethyl-7-sulfo-1H-benzo[e]indol-2(3H)-ylidene)ethylidene)-5-(1-methoxy-2-methyl-1-oxopropan-2-yl)cyclohex-1-enyl)vinyl)-3-ethyl-1,1-dimethyl-1H-benzo[e]indolium-7-sulfonate | 849 nm/ 883 nm (DMSO) |

TABLE 1-continued

| Compound | Structural Formula | Name | Absorption/Emission wavelength (Solvent) |
|---|---|---|---|
| Compound H (Example 8) | | 4-((E)-6-((E)-2-(3-ethyl-7-methoxy-1,1-dimethyl-1H-benzo[e]indol-2(3H)-ylidene)ethylidene)-2-((E)-2-(3-ethyl-7-methoxy-1,1-dimethyl-1H-benzo[e]indolium-2-yl)vinyl)-4-(1-methoxy-2-methyl-1-oxopropan-2-yl)cyclohex-1-enylthio)benzoate | 857 nm/ 900 nm (DMSO) |
| Compound I (Example 9) | | 2-((E)-2-((E)-2-(4-(2-aminoethylcarbamoyl)phenylthio)-3-((E)-2-(3-ethyl-7-methoxy-1,1-dimethyl-1H-benzo[e]indol-2(3H)-ylidene)ethylidene)-5-(1-methoxy-2-methyl-1-oxopropan-2-yl)cyclohex-1-enyl)vinyl)-3-ethyl-7-methoxy-1,1-dimethyl-1H-benzo[e]indolium iodide | 857/ 889 nm (DMSO) |
| Compound J (Example 10) | | 3-ethyl-2-((E)-2-((E)-3-((E)-2-(3-ethyl-7-methoxy-1,1-dimethyl-1H-benzo[e]indol-2(3H)-ylidene)ethylidene)-2-(4-(2-isothiocyantoethylcarbamoyl)phenylthio)-5-(1-methoxy-2-methyl-1-oxopropan-2-yl)cyclohex-1-enyl)vinyl)-7-methoxy-1,1-dimethyl-1H-benzo[e]indolium iodide | 856/ 905 nm (DMSO) |

TABLE 1-continued

| Compound | Structural Formula | Name | Absorption/Emission wavelength (Solvent) |
|---|---|---|---|
| Compound K (Example 11) | | 2-((E)-2-((E)-2-(4-(2-aminoethylcarbamoyl)phenylthio)-3-((E)-2-(3-ethyl-7-methoxy-1,1-dimethyl-1H-benzo[e]indol-2(3H)-ylidene)ethylidene)cyclohex-1-enyl)vinyl)-3-ethyl-7-methoxy-1,1-dimethyl-1H-benzo[e]indolium iodide | 857 nm/ 901 nm (DMSO) |
| Compound L (Example 12) | | 2-((E)-2-((E)-2-(4-(2-aminoethylcarbamoyl)phenylthio)-5-tert-butyl-3-((E)-2-(3-ethyl-7-methoxy-1,1-dimethyl-1H-benzo[e]indol-2(3H)-ylidene)ethylidene)cyclohex-1-enyl)vinyl)-3-ethyl-7-methoxy-1,1-dimethyl-1H-benzo[e]indolium iodide | 857 nm/ 896 nm (DMSO) |

As can be confirmed in the above table, the cited compounds of the present invention have an absorption wavelength of 830 nm or more, and preferably 855 nm or more, and an emission wavelength of 860 nm, and preferably 890 nm.

Meanwhile, the compounds represented by Chemical Formula 1 according to the present invention may be prepared by various methods, and for example, may be prepared by Synthesis Schemes 1 to 6 below.

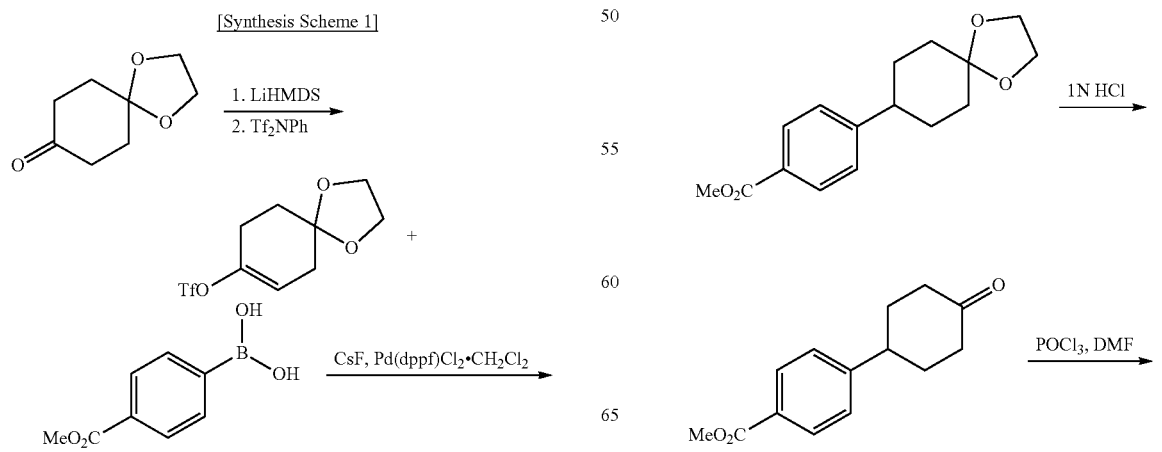

[Synthesis Scheme 1]

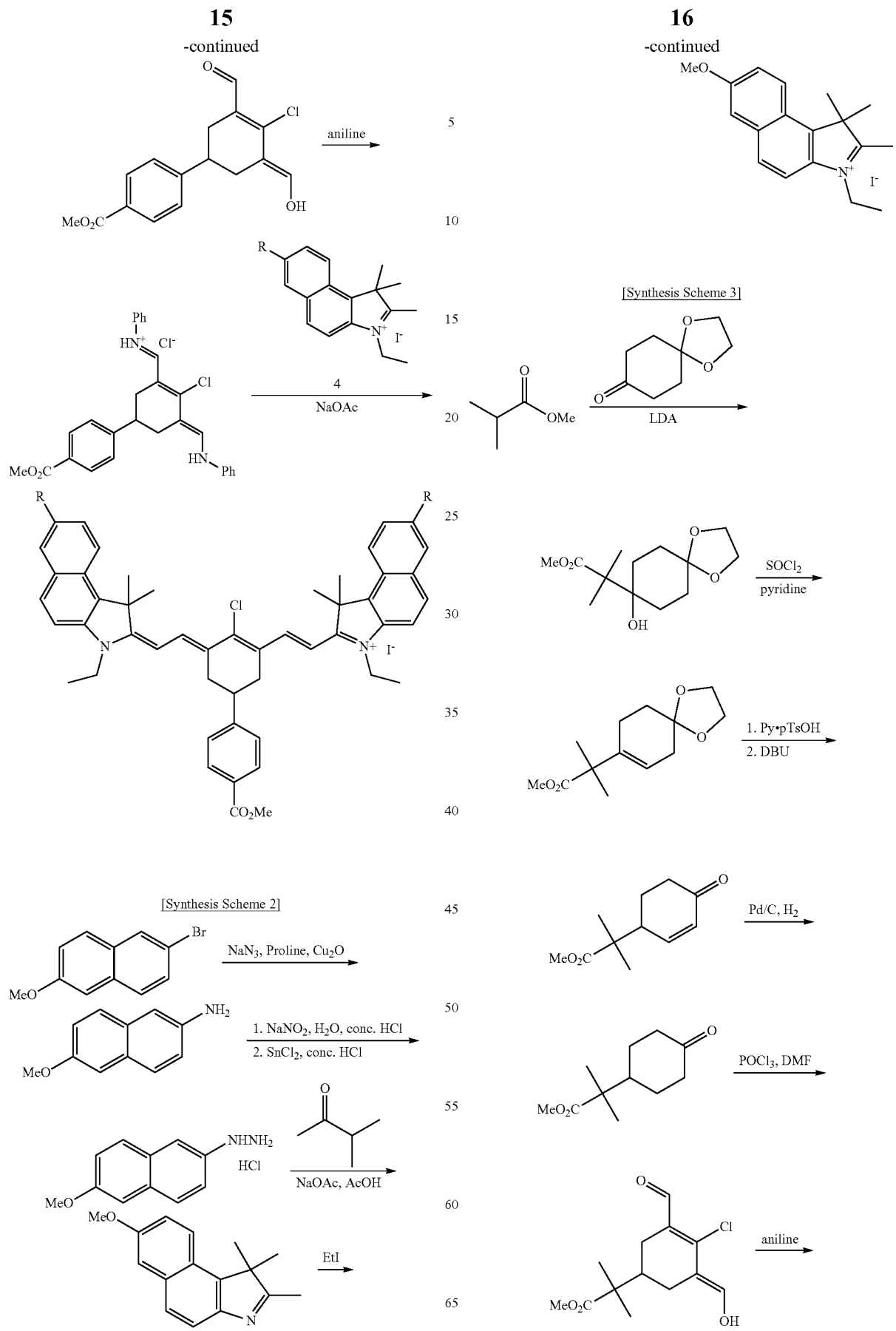

-continued
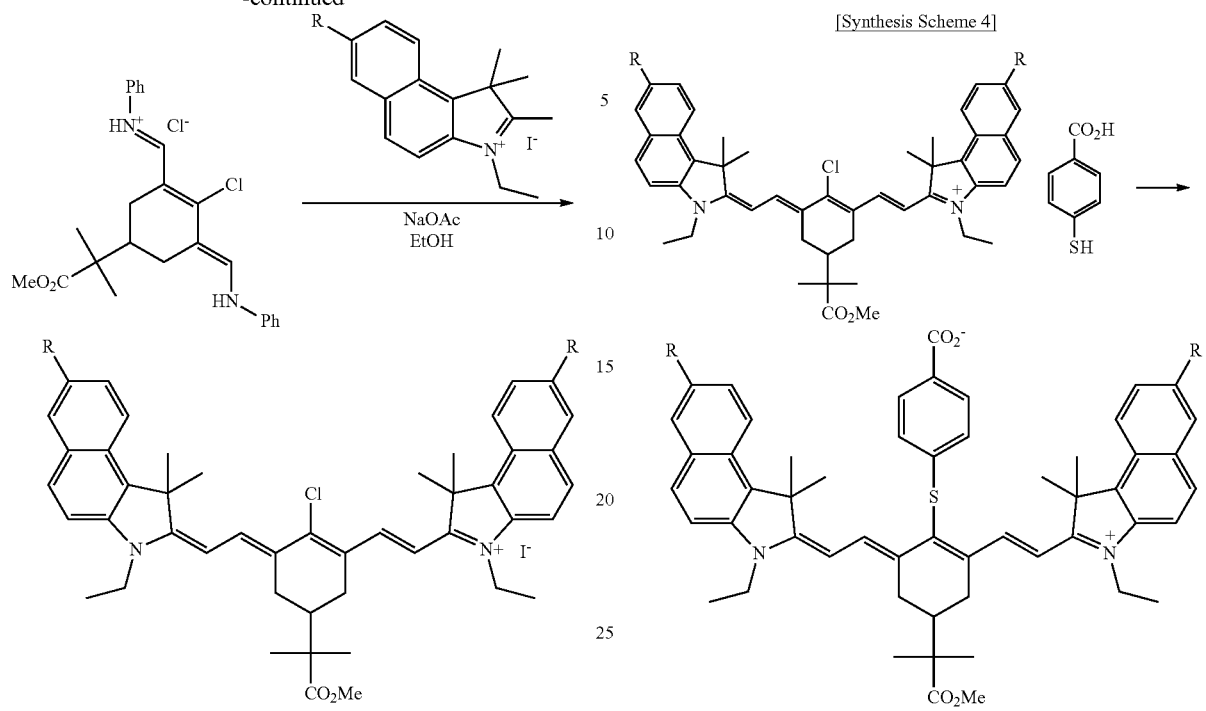
[Synthesis Scheme 4]
[Synthesis Scheme 5]
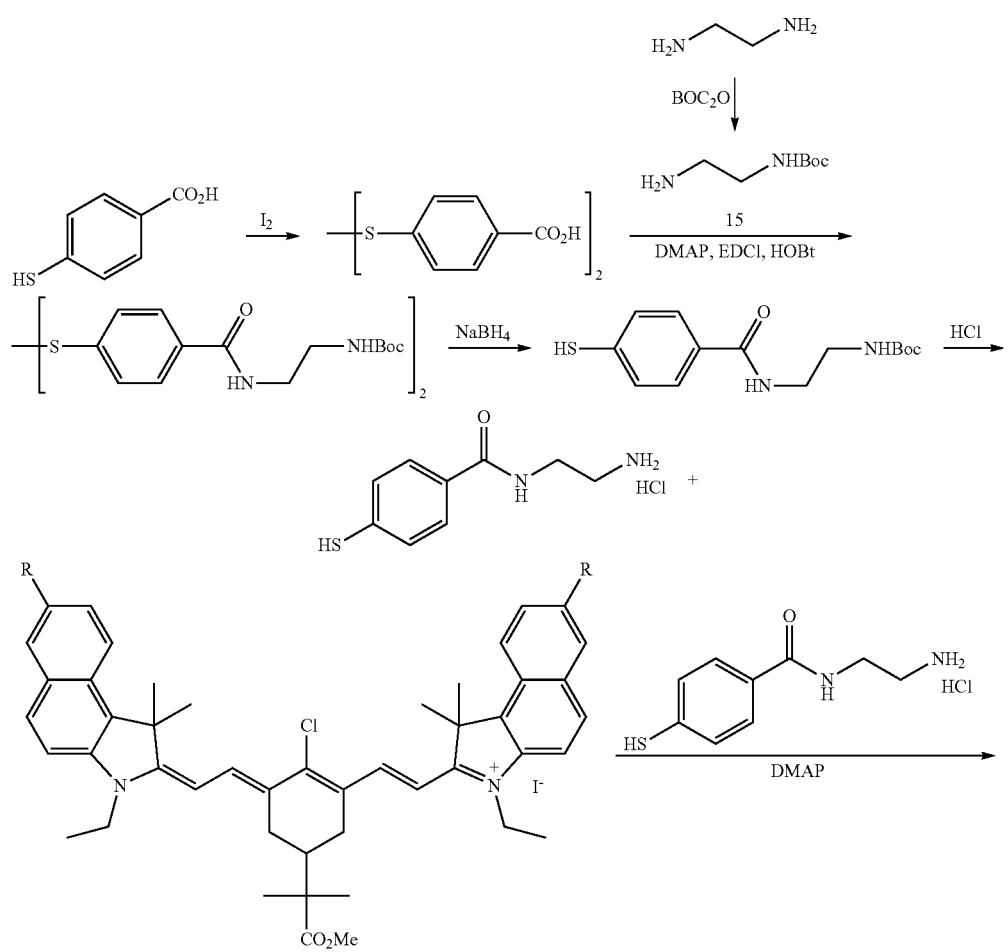

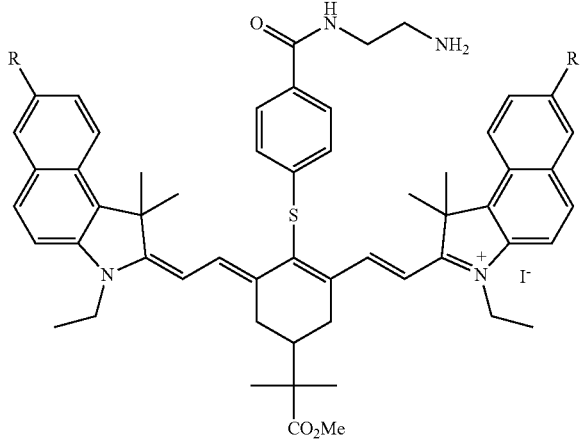

[Synthesis Scheme 6]

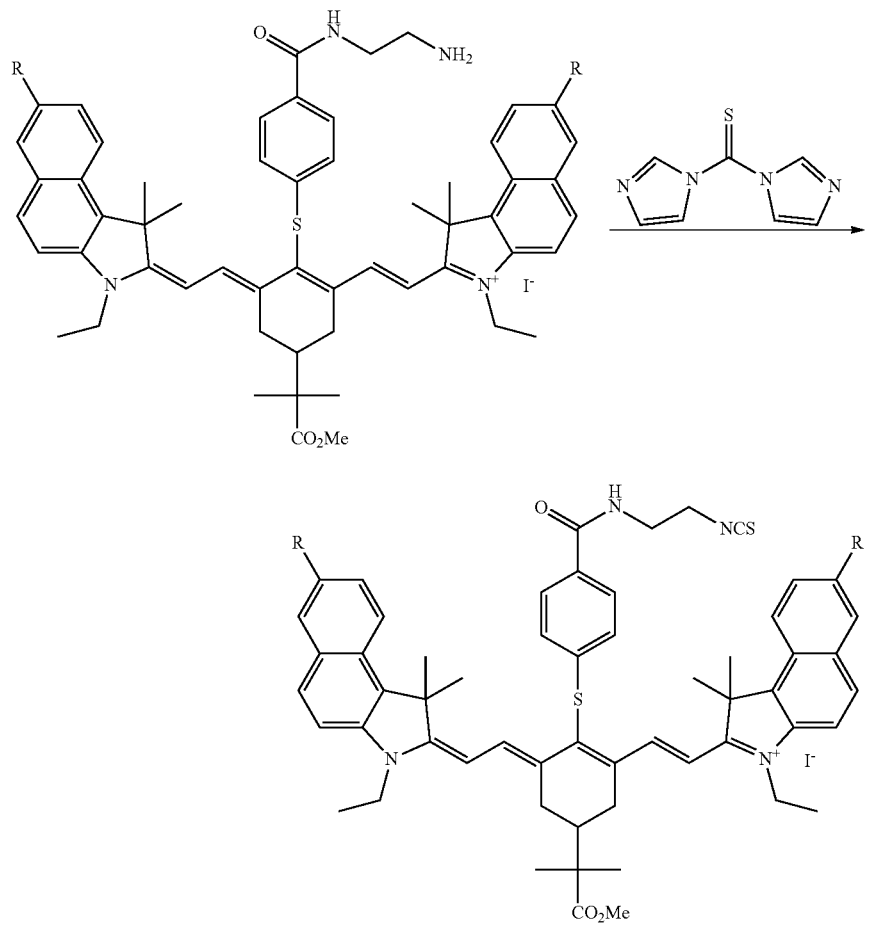

In another embodiment, the present invention relates to a near-infrared fluorescent constant medium containing, as an active ingredient, a compound of Chemical Formula 1 or a pharmaceutically acceptable salt thereof.

The near-infrared fluorescent contrast medium of the present invention is a contrast medium emitting fluorescence in a near-infrared region.

The near-infrared fluorescent contrast medium of the present invention may contain a compound of Chemical Formula 1 or a pharmaceutically acceptable salt thereof alone or in combination. The pharmaceutically acceptable salt thereof may include an ammonium salt, a potassium salt, an iodine salt, and the like, but the present invention is not limited thereto.

The near-infrared fluorescent contrast medium of the present invention may be a near-infrared fluorescent contrast medium for tumor imaging or angiography.

The near-infrared fluorescent contrast medium of the present invention preferably comprises core-shell structured particles in a solution, each of the particles includes: a core containing the compound or the pharmaceutically acceptable salt thereof; and a shell containing a lipid.

Here, the core-shell nanoparticles may have a size of 10-500 nm, and more preferably 10-100 nm. When the particles are nanometer-sized, the targeting of such particles to cancer cells increases the intensity of fluorescence (enhanced permeability and retention (EPR)) and reduces photo-beaching, thereby showing excellent optical properties.

The core-shell particles may have a size of 10-500 nm.

The compound of Chemical Formula 1 contained in the near-infrared fluorescent contrast medium of the present invention has longer absorption and emission wavelengths than existing known materials, and thus can further increase the imaging depth and can diagnose and operate deep cancer cells or tissues when used as a contrast medium.

Meanwhile, the contrast medium may contain the compound of Chemical Formula 1 or a pharmaceutically acceptable salt thereof, which is dispersed or dissolved in a solvent, such as distilled water for injection, pharmaceutical saline, or Ringer's solution. If necessary, a pharmaceutically acceptable additive, such as a carrier or an excipient, may be added. Such an additive includes a pharmacologically acceptable electrolyte, a buffer, a detergent, an osmotic pressure-regulating substance, and a material improving stability and solubility (e.g., cyclodextrin, liposomes, etc.). Various additives commonly used in related fields may also be used. The near-infrared fluorescent contrast medium of the present invention is preferably prepared through a sterilization process when intended for pharmaceutical use.

In still another embodiment, the present invention relates to a method for preparing a near-infrared fluorescent contrast medium, the method including the steps of: dissolving the compound of any one of claims 1 to 8 or a pharmaceutically acceptable salt thereof in an organic solvent; adding dropwise the obtained dissolved product to an aqueous solution, in which a lipid having a primary amine group is dispersed, to prepare an emulsion, and then removing the organic solvent from the emulsion to manufacture core-shell nanoparticles; and modifying a surface of the manufactured core-shell nanoparticles with sulfo-succinimidyl 4-(N-maleimidomethyl)cyclohexane-1-carboxylate (sulfo-SMCC).

The preparation method will be described step by step in detail.

First, the compound represented by Chemical Formula or a pharmaceutically acceptable salt thereof is dissolved in an organic solvent. The reason is that the compound represented by Chemical Formula 1 does not readily dissolve in water.

The organic solvent is preferably a volatile organic solvent to facilitate subsequent removal of the solvent later. Examples of the volatile organic solvent may include methanol, ethanol, acetone, acetonitrile, dichloromethane, propanol, carbon tetrachloride, chloromethyl, DMSO, DMF, THF, or mixtures thereof, but are not limited thereto.

Then, the obtained dissolved product is added dropwise to to an aqueous solution, in which a lipid having a primary amine group is dispersed, to prepare an emulsion, and then an organic solvent is removed from the emulsion to manufacture core-shell nanoparticles.

An example of the lipid having a primary amine group is a phospholipid, and more specifically, may be at least one selected from the group consisting of DPPC 1,2-didecanoyl-sn-glycero-3-phosphocholine), DEPE (1,2-dierucoyl-sn-glycero-3-phosphoethanolamine), DLPE (1,2-dilauroyl-sn-glycero-3-phosphoethanolamine), DMPE (1,2-dimyristoyl-sn-glycero-3-phosphoethanolamine), DOPE (1,2-dipalmitoyl-sn-glycero-3-phosphoethanolamine), DSPE (1,2-distearoyl-sn-glycero-3-phosphoethanolamine), and POPE (1-palmitoyl-2-oleoyl-sn-glycero-3-phosphoethanolamine). The reason why the lipid must have a primary amine group is to introduce a cancer cell-specific and recognizable antibody, peptide, or the like through chemical bonding.

The core-shell structured nanoparticles have a size of preferably 10-500 nm and more preferably 10-100 nm. When the particles are nanometer-sized, the targeting of such particles to cancer cells increases the intensity of fluorescence (enhanced permeability and retention (EPR)) and reduces photo-beaching, thereby showing excellent optical properties.

Then, a surface of the manufactured core-shell nanoparticles is modified with at least one of a maleimide group, a carboxyl group, or an azide group. Here, the surface modification may be performed using at least one modifier selected from the group consisting of sulfo-succinimidyl 4-(N-maleimidomethyl)cyclohexane-1-carboxylate (sulfo-SMCC), 3,6,9-trioxadodec-11-yn-1-ol mesylate, and 11-azido-3,6,9-trioxa-1-undecanol mesylate.

On the other hand, the contrast medium may be administered to a living body through injection, spraying, coating, or intravenous (intravenous, arterial), oral, intraperitoneal, transdermal, subcutaneous, intracapsular, or intratumoral administration. Preferably, the agent is administered in the form of an aqueous formulation, emulsion, or suspension in a blood vessel.

The administration of the near-infrared fluorescent contrast medium of the present invention is not particularly limited to enabling the examination of a site which is to be finally diagnosed by administration. The administration is appropriately controlled depending on the kind of compound that emits the near-infrared fluorescence to be used, and the age, body weight, and target organ of a subject. Typically, the dosage is 0.1-100 mg/kg body weight, preferably 0.5-20 mg/kg body weight, on the basis of the amount of the compound.

The contrast medium of the present invention is also appropriate for use in various animals other than humans. The dosage form, route, and dose are suitably determined depending on the weight and disease state of a target animal.

The near-infrared fluorescent contrast medium of the present invention is generally administered to a detection target, and the detection target is exposed to an excitation light from the excitation light source. Thereafter, the fluorescence from the near-infrared fluorescent contrast medium, caused by the excitation light, is detected using a fluorescence detector. The wavelength for excitation varies depending on the near-infrared fluorescent contrast medium that is used. The compound of the present invention effectively emits fluorescence in the near-infrared region, and thus has excellent bio-transmission.

Example 1

2-((E)-2-((E)-2-chloro-3-((E)-2-(3-ethyl-1,1-dimethyl-7-sulfo-1H-benzo[e]indo-1-2(3H)-ylidene)ethylidene)-5-(4-(methoxycarbonyl)phenyl)cyclohex-1-enyl)vinyl)-3-ethyl-1,1-dimethyl-1H-benzo[e]indolium-7-sulfonate

[Compound A]

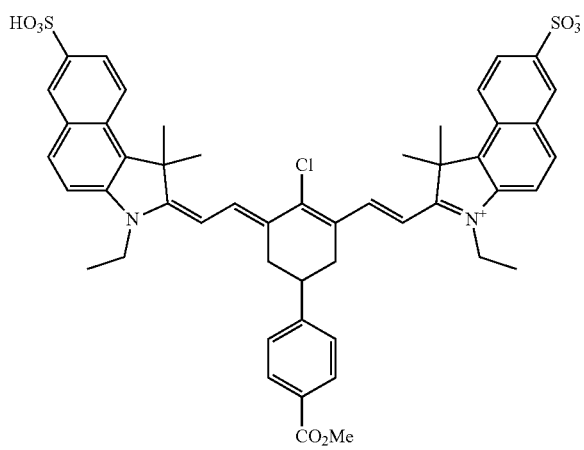

1-1: Synthesis of 1,1,2-trimethyl-1H-benzo[e]indole-7-sulfonic acid

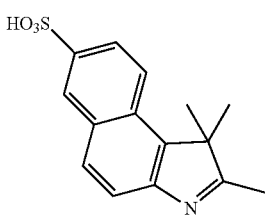 [SMILES: CC1=Nc2ccc3cc(S(=O)(=O)O)ccc3c2C1(C)C]

A mixture of 1,1,2-trimethyl-1H-benzo[e]indole (1.00 g, 4.78 mmol) and sulfuric acid (3.69 ml, 69.3 mmol) was stirred at 140° C. for 1 hour. After the stirred solution was cooled to room temperature, an ice-water mixture was added thereto, and the mixed solution was adjusted to pH 3 using an aqueous solution of 6 N NaOH. The generated solid was filtered and then washed with water and Et$_2$OH. The obtained solid was dried in vacuo to give a white solid of 1,1,2-trimethyl-1H-benzo[e]indole-7-sulfonic acid (682 mg, 2.36 mmol, 49.3%).

$^1$H-NMR (DMSO-d6, Varian 400 MHz): δ1.63 (6H, s), 2.62 (3H, d, J=6.4 Hz), 7.78 (1H, d, J=8.4 Hz), 7.87 (1H, d, J=8.4 Hz), 8.14-8.18 (1H, m), 8.21 (1H, d, J=8.8 Hz), 8.32 (1H, s).

1-2: Synthesis of 3-ethyl-1,1,2-trimethyl-1H-benzo[e]indolium-7-sulfonate

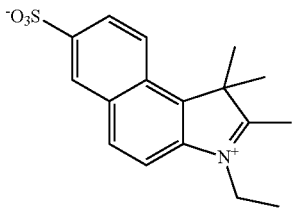

After 1,2-trimethyl-1H-benzo[e]indole-7-sulfonic acid (100 mg, 0.346 mmol), iodoethane (0.279 ml, 3.46 mmol), and K$_2$CO$_3$ (48 mg, 0.346 mmol) were added to dimethylformamide (1 ml), the mixture was stirred at 100° C. for 6 hours. The stirred solution was cooled to room temperature and then concentrated in vacuo, and the concentrated solution was recrystallized by ethanol to give 3-ethyl-1,1,2-trimethyl-1H-benzo[e]indolium-7-sulfonate (190 mg, 0.429 mmol). The obtained compound was used for a subsequent reaction without separate purification.

$^1$H-NMR (DMSO-d6, Varian 400 MHz): δ 1.50 (3H, t, J=7.2 Hz), 1.75 (6H, s), 2.92 (3H, s), 4.61 (2H, q, J=7.3 Hz), 7.95 (1H, d, J=8.4 Hz), 8.15 (1H, d, J=8.8 Hz), 8.32-8.37 (2H, m), 8.41 (1H, s).

1-3: Synthesis of 1,4-dioxaspiro[4.5]dec-7-en-8-yl trifluoromethanesulfonate

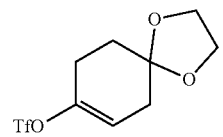 [SMILES: O=S(=O)(OC1=CCC2(CC1)OCCO2)C(F)(F)F]

After 1,4-dioxaspiro[4.5]decan-8-one (2.00 g, 12.8 mmol) was dissolved in tetrahydrofuran and then cooled to −78° C., a solution of 1.06 M lithium bis(trimethylsilyl)amide/tetrahydrofuran (14.5 ml, 15.4 mmol) was added dropwise thereto. The reacted solution was stirred at −78° C. for 2 hours, and then a solution of 1,1,1-trifluoro-N-phenyl-N-(trifluoromethylsulfonyl) methanesulfonamide (4.80 g, 13.5 mmol) dissolved in tetrahydrofuran (10 ml) was added dropwise thereto at −78° C. After the temperature of the reacted solution was slowly raised to 0° C., the reacted solution was stirred at 0° C. for 2 hours. Then, water was added to the reacted solution, followed by extraction with ethyl acetate. The separated organic layer was washed with an aqueous solution of saturated NaCl, dried over sodium sulfate, and then concentrated in vacuo. The concentrated solution was purified using silica gel column chromatography (hexane:ethylacetate=9:1) to give a yellow oil of 1,4-dioxaspiro[4.5]dec-7-en-8-yl trifluoromethanesulfonate (3.55 g, 12.3 mmol, 96%).

$^1$H-NMR (CDCl3, Varian 400 MHz): δ 1.91 (2H, t, J=6.6 Hz), 2.40-2.42 (2H, m), 2.53-2.56 (2H, m), 3.99 (4H, s), 5.65-5.67 (1H, m).

1-4: Synthesis of methyl 4-(1,4-dioxaspiro[4.5]dec-7-en-8-yl)benzoate

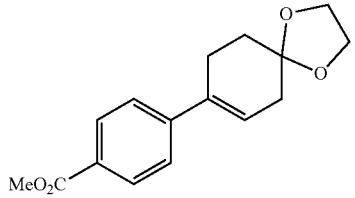 [SMILES: COC(=O)c1ccc(C2=CCC3(CC2)OCCO3)cc1]

CsF (1.58 g, 10.4 mmol) and a PdCl₂ (dppf)-CH₂Cl₂ additive (142 mg, 0.173 mmol) were added to 1,4-dioxaspiro[4.5]dec-7-en-8-yl trifluoromethanesulfonate (1.00 g, 3.47 mmol) dissolved in 1,4-dioxane (17 ml), followed by heating at 90° C. for 3 hours. After the reacted solution was concentrated in vacuo, the concentrated solution was dissolved in ethyl acetate and the dissolved solution was filtered through celite. The filtered solution was again concentrated in vacuo, and then the concentrated solution was purified (hexane:ethyl acetate=4:1) using silica gel column chromatography to give a white solid of methyl 4-(1,4-dioxaspiro[4.5]dec-7-en-8-yl)benzoate (697 mg, 2.54 mmol, 73.2%).

¹H-NMR (CDCl3, Varian 400 MHz): δ1.94 (2H, t, J=6.4 Hz), 2.48-2.52 (2H, m), 2.66-2.70 (2H, m), 3.91 (3H, s), 4.03 (4H, s), 6.00-6.13 (1H, m), 7.45 (2H, d, J=8.4 Hz), 7.97 (2H, d, J=6.0 Hz).

1-5: Synthesis of methyl 4-(1,4-dioxaspiro[4.5]decan-8-yl)benzoate

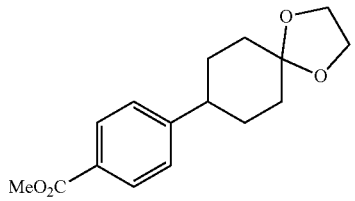 [SMILES: COC(=O)c1ccc(C2CCC3(CC2)OCCO3)cc1]

Methyl 4-(1,4-dioxaspiro[4.5]dec-7-en-8-yl)benzoate (697 mg, 2.54 mmol) and 10% Pd/C (174 mg) were added to a mixture (25.5 mL, 1:2) of ethyl acetate and methanol, followed by stirring at room temperature for 3 hours under a hydrogen atmosphere at a pressure of 45 psi. The reacted solution was dissolved through celite, and then the filtered solution was concentrated in vacuo to give a gray solid of methyl 4-(1,4-dioxaspiro[4.5]decan-8-yl)benzoate (675 mg, 2.44 mmol, 96%). The obtained compound was used for a subsequent reaction without separate purification.

¹H-NMR (CDCl3, Varian 400 MHz): δ1.66-1.88 (8H, m), 2.60-2.65 (1H, m), 3.90 (3H, s), 3.99 (4H, s), 7.31 (2H, d, J=8.0 Hz), 7.96 (2H, d, J=8.0 Hz).

1-6: Synthesis of methyl 4-(4-oxocyclohexyl)benzoate

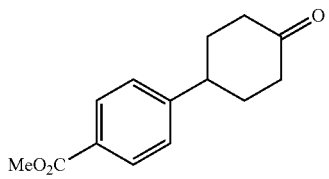 [SMILES: COC(=O)c1ccc(C2CCC(=O)CC2)cc1]

1 M hydrochloric acid (6.11 ml, 6.11 mmol) was added dropwise to methyl 4-(1,4-dioxaspiro[4.5]decan-8-yl)benzoate (675 mg, 2.44 mmol) dissolved in tetrahydrofuran (12 ml) at room temperature. The reacted solution was stirred at room temperature for 39 hours and then concentrated in vacuo. The concentrated solution was dissolved in ethyl acetate and then washed with an aqueous solution of saturated sodium bicarbonate. The separated organic layer was dried over sodium sulfate, and then concentrated in vacuo. The concentrated solution was purified using silica gel column chromatograph (hexane:ethyl acetate=4:1) to give a white solid of methyl 4-(4-oxocyclohexyl)benzoate (352 mg, 1.52 mmol, 62.1%).

1H-NMR (CDCl3, Varian 400 MHz): δ1.91-2.02 (2H, m), 2.20-2.26 (2H, m), 2.50-2.56 (4H, m), 3.09 (1H, t, J=12.2 Hz), 3.91 (3H, s), 7.32 (2H, d, J=8.0 Hz), 8.00 (2H, d, J=8.0 Hz).

1-7: Synthesis of (E)-methyl 4-(4-chloro-3-formyl-5-(hydroxymethylene)cyclohex-3-enyl)benzoate

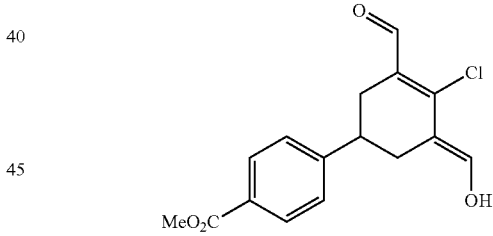

Phosphoryl trichloride (0.161 ml, 1.72 mmol) was slowly added dropwise to anhydrous dimethylformamide (0.167 ml, 2.15 mmol) cooled to 0° C. After the reacted solution was stirred at room temperature for 30 minutes, a solution of methyl 4-(4-oxocyclohexyl)benzoate (100 mg, 0.431 mmol) diluted in dimethylformamide (2.15 ml) was added dropwise to the reacted solution. The reaction solution was stirred at 55° C. for 2 hours, and then an ice-water mixture was added thereto. After the mixed solution was stirred at room temperature for 24 hours, the generated precipitate was filtered and then washed with diisopropyl ether. The obtained solid was dried in vacuo to give a yellow solid of (E)-methyl 4-(4-chloro-3-formyl-5-(hydroxymethylene)cyclohex-3-enyl)benzoate (50 mg, 0.163 mmol, 37.9%).

¹H-NMR: (DMSO-d6, Varian 400 MHz): δ2.35-2.42 (2H, m), 2.73-2.94 (3H, m), 3.85 (3H, s), 7.46 (2H, d, J=8.0 Hz), 7.91 (2H, d, J=8.0 Hz), 11.05 (1H, s).

1-8: Synthesis of (E)-N-(((E)-2-chloro-5-(4-(methoxycarbonyl)phenyl)-3-((phenylamino)methylene)cyclohex-1-enyl)methylene)benzenaminium chloride

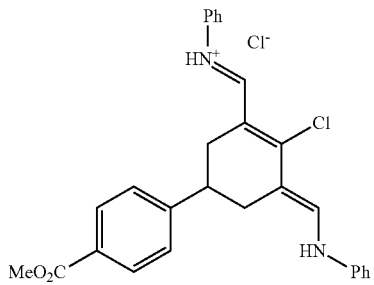 [SMILES: COC(=O)c1ccc(C2CC(/C=[NH+]/c3ccccc3)=C(Cl)C(=C/Nc3ccccc3)/C2)cc1 ; [Cl-]]

After a solution of (E)-methyl 4-(4-chloro-3-formyl-5-(hydroxymethylene)cyclohex-3-enyl)benzoate (50 mg, 0.163 mmol) dissolved in ethanol and dimethylformamide (0.2 ml) was cooled to 0° C., concentrated hydrochloric acid (0.120 ml, 1.39 mmol) was added dropwise thereto. Aniline (0.033 ml, 0.359 mmol) was added dropwise to the reacted solution at 0° C. and then stirred at 0° C. for 30 minutes. The reacted solution was added to an ice-water mixture, after which the generated solid was filtered and washed with water and diisopropyl ether. The filtered solid was dried in vacuo to give a violet solid of (E)-N-(((E)-2-chloro-5-(4-(methoxycarbonyl)phenyl)-3-((phenylamino)methylene)cyclohex-1-enyl)methylene)benzenaminium chloride (69.8 mg, 0.141 mmol, 87%).

$^1$H-NMR (DMSO-d6, Varian 400 MHz): δ2.73 (2H, t, J=13.2 Hz), 3.16 (1H, t, J=11.6 Hz), 3.25 (2H, d, J=14.8 Hz), 3.66 (1H, brs), 3.87 (3H, s), 7.25-7.30 (2H, m), 7.44-7.48 (4H, m), 7.54-7.59 (4H, m), 7.68 (2H, d, J=7.6 Hz), 8.01 (2H, d, J=7.6 Hz), 8.62 (2H, s), 11.29 (1H, brs).

1-9: Synthesis of 2-((E)-2-((E)-2-chloro-3-((E)-2-(3-ethyl-1,1-dimethyl-7-sulfo-1H-benzo[e]indol-2(3H)-ylidene)ethylidene)-5-(4-(methoxycarbonyl)phenyl)cyclohex-1-enyl)vinyl)-3-ethyl-1,1-dimethyl-1H-benzo[e]indolium-7-sulfonate

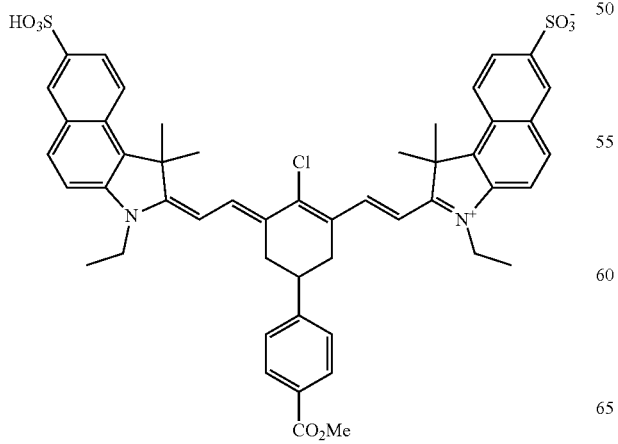

After a solution of sodium acetate (13 mg, 0.162 mmol) was added to a solution of (E)-N-(((E)-2-chloro-5-(4-(methoxycarbonyl)phenyl)-3-((phenylamino)methylene)cyclohex-1-enyl)methylene)benzenaminium chloride (20 mg, 0.041 mmol) and 3-ethyl-1,1,2-trimethyl-1H-benzo[e]indolium-7-sulfonate (54 mg, 0.122 mmol), dissolved in ethanol (0.8 ml), the solution was heated at 90° C. for 3 hours. The reacted solution was concentrated in vacuo, and then the concentrated solution was purified using silica gel column chromatography (dichloromethane:methanol:acetic acid=4:1:0.05) to give a dark blue solid of 2-((E)-2-((E)-2-chloro-3-((E)-2-(3-ethyl-1,1-dimethyl-7-sulfo-1H-benzo[e]indol-2(3H)-ylidene)ethylidene)-5-(4-(methoxycarbonyl)phenyl)cyclohex-1-enyl)vinyl)-3-ethyl-1,1-dimethyl-1H-benzo[e]indolium-7-sulfonate (21.9 g, 0.024 mmol, 59.7%).

Example 2

7-bromo-2-((E)-2-((E)-3-((E)-2-(7-bromo-3-ethyl-1,1-dimethyl-1H-benzo[e]indol-2(3H)-ylidene)ethylidene)-2-chloro-5-(4-(methoxycarbonyl)phenyl)cyclohex-1-enyl)vinyl)-3-ethyl-1,1-dimethyl-1H-benzo[e]indolium iodide

[Compound B]

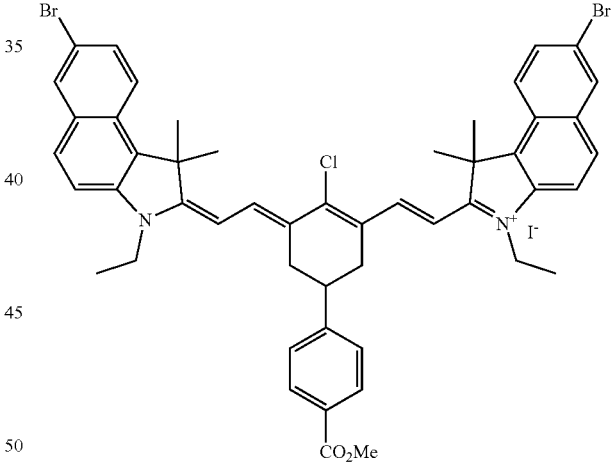

2-1: Synthesis of 7-bromo-3-ethyl-1,1,2-trimethyl-1H-benzo[e]indolium iodide

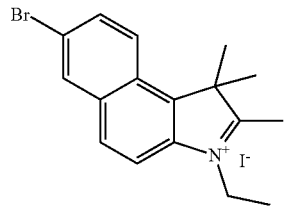 [SMILES: CC[N+]1=C(C)C(C)(C)c2c1ccc1cc(Br)ccc21 ; [I-]]

A mixture of 7-bromo-1,1,2-trimethyl-1H-benzo[e]indole (300 mg, 1.04 mmol) dissolved in acetonitrile (1 ml), and iodoethane (0.252 ml, 3.12 mmol) was heated at 90° C. for 11 hours. After the reacted solution was cooled to room temperature, the generated solid was filtered, and then washed with acetonitrile and Et$_2$O to give a gray solid of 7-bromo-3-ethyl-1,1,2-trimethyl-1H-benzo[e]indolium iodide (343 mg, 0.772 mmol, 74.2%).

$^1$H-NMR (DMSO-d6, Varian 400 MHz): δ1.50 (3H, t, J=7.2 Hz), 1.75 (6H, s), 2.93 (3H, s), 4.61 (2H, q, J=7.2 Hz), 7.88 (1H, d, J=8.8 Hz), 8.23 (1H, d, J=9.2 Hz), 8.30 (1H, d, J=8.8 Hz), 8.36 (1H, d, J=9.2 Hz), 8.55 (1H, s).

Synthesis of 2-2.7-bromo-2-((E)-2-((E)-3-((E)-2-(7-bromo-3-ethyl-1,1-dimethyl-1H-benzo[e]indol-2(3H)-ylidene)ethylidene)-2-chloro-5-(4-(methoxycarbonyl)phenyl)cyclohex-1-enyl)vinyl)-3-ethyl-1,1-dimethyl-1H-benzo[e]indolium iodide

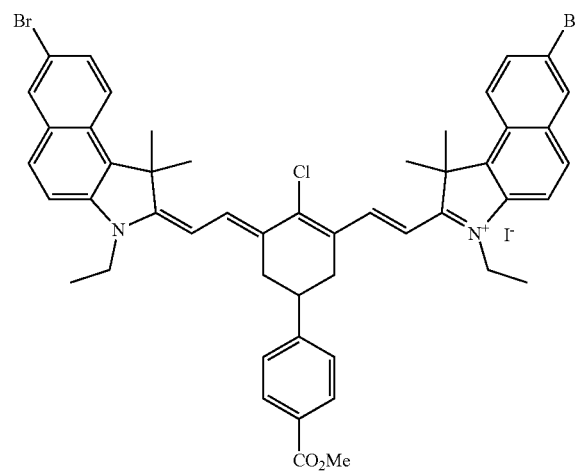 [SMILES: CCN1/C(=C/C=C2\CC(c3ccc(C(=O)OC)cc3)CC(/C=C/C3=[N+](CC)c4ccc5cc(Br)ccc5c4C3(C)C)=C2Cl)C(C)(C)c2c1ccc1cc(Br)ccc21 ; [I-]]

After a solution of sodium acetate (9.98 mg, 0.122 mmol) was added to a solution of (E)-N-(((E)-2-chloro-5-(4-(methoxycarbonyl)phenyl)-3-((phenylamino)methylene)cyclohex-1-enyl)methylene)benzenaminium chloride (0.02 g, 0.041 mmol) and 7-bromo-3-ethyl-1,1,2-trimethyl-1H-benzo[e]indolium (40 mg, 0.089 mmol), dissolved in ethanol (0.811 ml), the solution was heated at 90° C. for 3 hours. The reacted solution was concentrated in vacuo, and then the concentrated solution was purified by silica gel column chromatography (dichloromethane:methanol:acetic acid=95:5) to give a dark blue solid of 7-bromo-2-((E)-2-((E)-3-((E)-2-(7-bromo-3-ethyl-1,1-dimethyl-1H-benzo[e]indol-2(3H)-ylidene)ethylidene)-2-chloro-5-(4-(methoxycarbonyl)phenyl)cyclohex-1-enyl)vinyl)-3-ethyl-1,1-dimethyl-1H-benzo[e]indolium iodide (32.5 mg, 0.032 mmol, 78%).

$^1$H-NMR (DMSO-d6, Varian 400 MHz): δ1.26 (6H, t, J=6.8 Hz), 1.91 (12H, s), 2.73 (2H, t, J=13.6 Hz), 3.15-3.20 (2H, m), 3.85 (3H, s), 4.28-4.34 (4H, m), 6.37 (2H, d, J=14.4 Hz), 7.64 (2H, d, J=8.0 Hz), 7.72 (2H, d, J=9.2 Hz), 7.79 (2H, d, J=8.8 Hz), 7.98 (2H, d, J=8.4 Hz), 8.07 (2H, d, J=8.8 Hz), 8.25 (2H, d, J=9.2 Hz), 8.34, (2H, s), 8.41 (2H, d, J=14.0 Hz).

Example 3

2-((E)-2-((E)-2-chloro-3-((E)-2-(3-ethyl-7-methoxy-1,1-dimethyl-1H-benzo[e]indol-2(3H)-ylidene)ethylidene)-5-(4-(methoxycarbonyl)phenyl)cyclohex-1-enyl)vinyl)-3-ethyl-7-methoxy-1,1-dimethyl-1H-benzo[e]indolium iodide—See Synthesis Schemes 1 and 2

[Compound C]

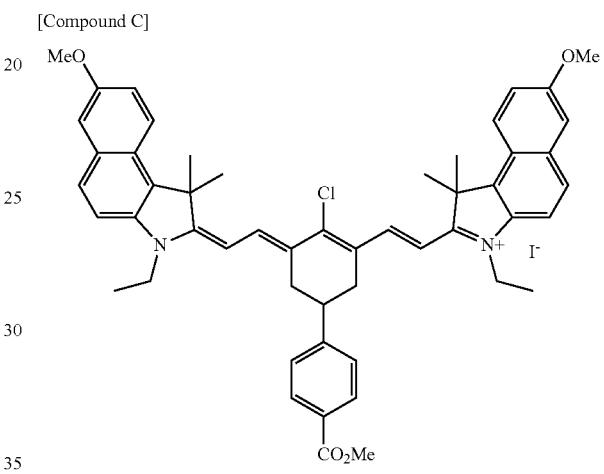

3-1: Synthesis of 6-methoxynaphthalene-2-amine

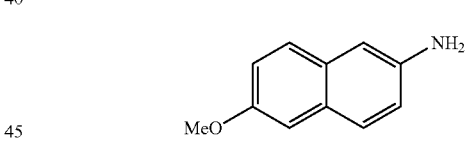

After 2-bromo-6-methoxynaphthalene (200 mg, 0.844 mmol), sodium azide (110 mg, 1.69 mmol), proline (126 mg, 1.10 mmol), and copper(I) oxide (121 mg, 0.844 mmol) were added to degassed DMSO (1.7 ml), this mixture was heated at 100° C. for 11 hours. The reacted solution was cooled to room temperature, and then ethyl acetate and water were introduced thereto. The mixed solution was filtered to remove solid, and then the filtered liquid was layer-separated. The separated organic layer was washed with an aqueous solution of saturated sodium bicarbonate, dried over sodium sulfate, and then concentrated in vacuo. The concentrated solution was purified by silica gel column chromatography (hexane:ethyl acetate=2:1) to give an orange solid of 6-methoxynaphthalene-2-amine (77.9 g, 0.450 mmol, 53.3%).

$^1$H-NMR (CDCl3, Varian 400 MHz): δ3.73 (2H, brs), 3.88 (3H, s), 6.93-6.97 (2H, m), 7.04-7.08 (2H, m), 7.51 (1H, d, J=8.8 Hz), 7.57 (1H, d, J=8.8 Hz)

3-2: Synthesis of (6-methoxynaphthalen-2-yl)hydrazine hydrochloride

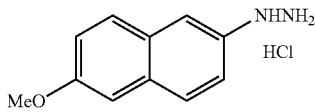 [SMILES: COc1ccc2cc(NN)ccc2c1 ; Cl]

A mixture of 6-methoxynaphthalene-2-amine (300 mg, 1.732 mmol), water (5.6 ml), and concentrated hydrochloric acid (2.17 ml, 26.0 mmol) was cooled to −6° C., and sodium nitride (137 mg, 1.99 mmol) dissolved in water (1.3 ml) was introduced thereto. After the reacted solution was stirred at 0° C. for 45 minutes, a solution of tin(II) chloride (657 mg, 3.46 mmol) dissolved in concentrated hydrochloric acid was slowly added dropwise thereto. The temperature of the reacted solution was slowly raised to room temperature, and then the generated solid was filtered, and washed with water and tert-butyl methyl ether. The obtained solid was dried in vacuo to give a gray solid of (6-methoxynaphthalen-2-yl)hydrazine hydrochloride (32 mg, 1.42 mmol, 82%).

$^1$H-NMR (DMSO-d6, Varian 400 MHz): δ3.84 (3H, s), 7.14 (1H, dd, J=8.8, 2.4 Hz), 7.20 (1H, d, J=9.6 Hz), 7.26 (2H, s), 7.65 (1H, d, J=8.8 Hz), 7.75 (1H, d, J=8.8 Hz), 8.40 (1H, brs), 10.31 (3H, brs).

3-3: Synthesis of 7-methoxy-1,1,2-trimethyl-1H-benzo[e]indole

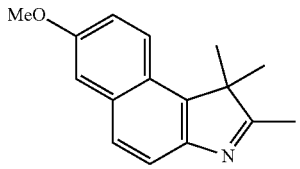 [SMILES: COc1ccc2c3c(ccc2c1)N=C(C)C3(C)C]

After 3-methylbutan-2-one (58 mg, 0.668 mmol) and sodium acetate (73 mg, 0.89 mmol) were added to a solution of (6-methoxynaphthalen-2-yl)hydrazine hydrochloride (100 mg, 0.445 mmol) dissolved in acetic acid (1 ml), this mixture was heated at 110° C. for 2 hours. The mixture was cooled, and then the reacted solution was diluted with toluene, and again concentrated to remove residual acetic acid. The concentrated solution was purified by silica gel column chromatography (hexane:ethyl acetate=2:1) to give a brown solid of 7-methoxy-1,1,2-trimethyl-1H-benzo[e]indole (67 mg, 0.280 mmol, 62.9%).

$^1$H-NMR (CDCl3, Varian 400 MHz): δ1.52 (6H, s), 2.37 (3H, s), 3.93 (3H, s), 7.21-7.26 (2H, m), 7.72-7.77 (2H, m), 7.92 (1H, d, J=9.2 Hz).

3-4: Synthesis of 3-ethyl-7-methoxy-1,1,2-trimethyl-1H-benzo[e]indolium iodide

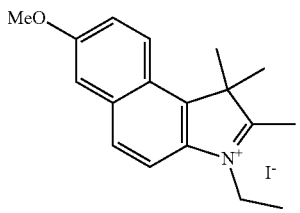 [SMILES: CC[N+]1=C(C)C(C)(C)c2c1ccc1cc(OC)ccc21 ; [I-]]

A mixture of acetonitrile (2.1 ml), ethyl iodide (0.507 ml, 6.27 mmol), and 7-methoxy-1,1,2-trimethyl-1H-benzo[e]indole (500 mg, 2.09 mmol) was refluxed for 12 hours, and then cooled to room temperature. After acetonitrile (2 ml) and ethyl ether (about 10 ml) were added to the reacted solution, the generated solid was filtered, and washed with ethyl acetate, to give a white solid of 3-ethyl-7-methoxy-1,1,2-trimethyl-1H-benzo[e]indolium iodide (733 mg, 1.85 mmol, 89%).

$^1$H-NMR (DMSO-d6, Varian 400 MHz): δ1.49 (3H, t, J=7.2 Hz), 1.73 (6H, s), 2.90 (3H, s), 3.94 (3H, s), 4.59 (2H, q, J=7.2 Hz), 7.42 (1H, dd, J=9.2, 1.2 Hz), 7.65 (1H, s), 8.09 (1H, d, J=8.8 Hz), 8.17 (1H, d, J=8.8 Hz), 8.30 (1H, d, J=9.2 Hz).

3-5: Synthesis of 2-((E)-2-((E)-2-chloro-3-((E)-2-(3-ethyl-7-methoxy-1,1-dimethyl-1H-benzo[e]indol-2(3H)-ylidene)ethylidene)-5-(4-(methoxycarbonyl)phenyl)cyclohex-1-enyl)vinyl)-3-ethyl-7-methoxy-1,1-dimethyl-1H-benzo[e]indolium iodide

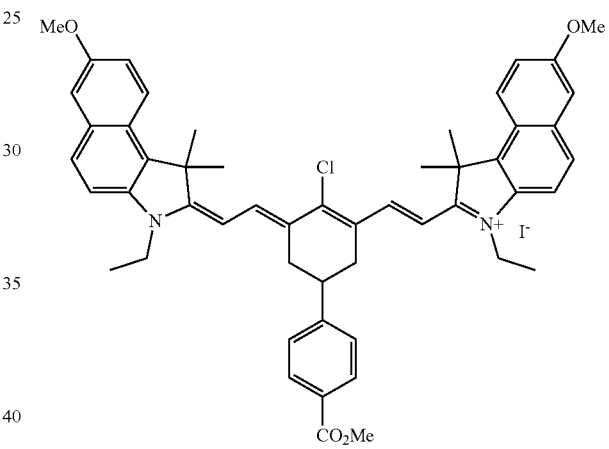

After a solution of sodium acetate (50 mg, 0.608 mmol) was added to a solution of (E)-N-(((E)-2-chloro-5-(4-(methoxycarbonyl)phenyl)-3-((phenylamino)methylene)cyclohex-1-enyl)methylene)benzenaminium chloride (100 mg, 0.203 mmol) and 3-ethyl-7-methoxy-1,1,2-trimethyl-1H-benzo[e]indolium iodide (176 mg, 0.446 mmol), dissolved in ethanol (4 ml), the solution was heated at 90° C. for 3 hours. The reacted solution was concentrated in vacuo, and then the concentrated solution was purified by silica gel column chromatography (dichloromethane:methanol:acetic acid=95:5) to give a dark blue solid of 2-((E)-2-((E)-2-chloro-3-((E)-2-(3-ethyl-7-methoxy-1,1-dimethyl-1H-benzo[e]indol-2(3H)-ylidene)ethylidene)-5-(4-(methoxycarbonyl)phenyl)cyclohex-1-enyl)vinyl)-3-ethyl-7-methoxy-1,1-dimethyl-1H-benzo[e]indolium iodide (162 mg, 0.174 mmol, 86%).

$^1$H-NMR (DMSO-d6, Varian 400 MHz): δ1.26 (3H, t, J=7.0 Hz), 1.90 (12H, s), 2.68-2.74 (2H, m), 3.10-3.17 (3H, m), 3.85 (3H, s), 3.87 (6H, s), 4.26-4.33 (4H, m), 6.31 (2H, d, J=14.0 Hz), 7.29 (2H, dd, J=9.2, 2.4 Hz), 7.48 (2H, d, J=2.0 Hz), 7.65 (4H, dd, J=17.6, 8.4 Hz), 7.96 and 7.98 (2H, ABq, JAB=6.2 Hz), 8.20 (2H, d, J=9.2 Hz), 8.37 (2H, d, J=14.4 Hz).

Example 4

2-((E)-2-((E)-2-chloro-3-((E)-2-(3-ethyl-1,1-dimethyl-7-sulfo-1H-benzo[e]indol-2(3H)-ylidene)ethylidene)-5-(1-methoxy-2-methyl-1-oxopropan-2-yl)cyclohex-1-enyl)vinyl)-3-ethyl-1,1-dimethyl-1H-benzo[e]indolium-7-sulfonate—See Synthesis Scheme 3

[Compound D]

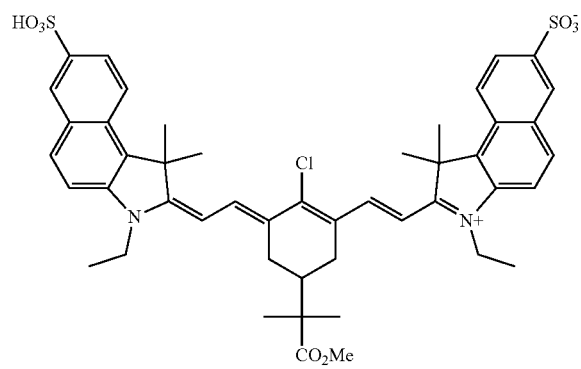

4-1: Synthesis of methyl 2-(8-hydroxy-1,4-dioxaspiro[4.5]decan-8-yl)-2-methylpropanate

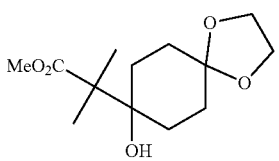 [SMILES: COC(=O)C(C)(C)C1(O)CCC2(CC1)OCCO2]

A solution of diisopropyl amine (6.98 ml, 49.0 mmol) diluted with tetrahydrofuran (40 ml) was cooled to −78° C., 2.5 M n-BuLi (19.6 ml, 49.0 mmol) was slowly added dropwise thereto. After methyl isobutyrate (1.12 ml, 9.79 mmol) was added to the reacted solution, followed by stirring at −78° C. for 20 minutes. A solution of 1,4-dioxaspiro[4.5]decan-8-one (1.53 g, 9.79 mmol) dissolved in tetrahydrofuran (9 ml) was added to the reacted solution at −78° C., followed by stirring at −78° C. for 3 hours. An aqueous solution of saturated ammonium chloride was added to the reacted solution, followed by extraction with ethyl acetate. The separated organic layer was washed with salt water, dried over anhydrous sodium sulfate, and then concentrated in vacuo. The concentrated solution was purified by silica gel column chromatography (hexane:ethyl acetate=3:2) to give a yellow oil of methyl 2-(8-hydroxy-1,4-dioxaspiro[4.5]decan-8-yl)-2-methylpropanate (1.53 g, 5.91 mmol, 60.4%).

$^1$H-NMR (CDCl3, Varian 400 MHz): δ1.25 (6H, s), 1.50-1.59 (4H, m), 1.72-1.79 (1H, m), 1.88-2.05 (3H, m), 2.52 (1H, t, J=6.8 Hz), 3.72 (3H, s), 3.91-3.97 (4H, m).

4-2: Synthesis of methyl 2-methyl-2-(1,4-dioxaspiro[4.5]dec-7-en-8-yl)propanate

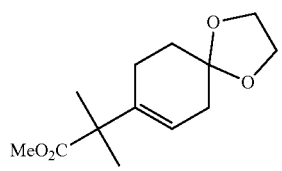

A mixture of methyl 2-(8-hydroxy-1,4-dioxaspiro[4.5]decan-8-yl)-2-methylpropanate (1.53 g, 5.91 mmol) and pyridine (59 ml) was cooled to 0° C., and then thionyl chloride (2.46 ml, 33.7 mmol) was slowly added dropwise. The reacted solution was stirred at room temperature for 14 hours, and then a water-ice mixture was added thereto, followed by extraction with dichloromethane. The separated organic layer was washed with salt water, dried over anhydrous sodium sulfate, and then concentrated in vacuo. The concentrated solution was purified by silica gel column chromatography (hexane:ethyl acetate=7:3) to give an organ oil of methyl 2-methyl-2-(1,4-dioxaspiro[4.5]dec-7-en-8-yl)propanate (1.15 g, 4.79 mmol, 81%).

$^1$H-NMR (CDCl3, Varian 400 MHz): δ1.32 (6H, s), 1.75 (2H, t, J=6.4 Hz), 2.14-2.18 (2H, m), 2.30-2.35 (2H, m), 3.67 (3H, s), 3.95-4.00 (4H, m), 5.50 (1H, s).

4-3: Synthesis of methyl 2-methyl-2-(4-oxocyclohex-2-enyl)propanate

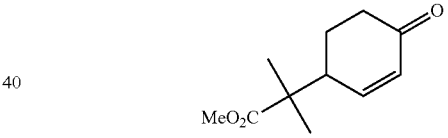

After pyridinium p-toluenesulfonate (1.46 g, 5.83 mmol) was added to a solution of methyl 2-methyl-2-(1,4-dioxaspiro[4.5]dec-7-en-8-yl)propanate (1.00 g, 4.16 mmol) dissolved in acetone (12.5 ml) and water (1.4 ml), this reacted solution was stirred at 100° C. for 3 days. After the reacted solution was concentrated in vacuo, the concentrated solution was diluted with ethyl acetate and then washed with water and salt water. The separated organic layer was dried over sodium sulfate, and then concentrated in vacuo. The concentrated solution was diluted with dichloromethane (13.9 ml), and then 1,8-diazabicyclo [5.4.0]undec-7-ene (1.694 ml, 11.24 mmol) was introduced thereto. The reacted solution was stirred at 50° C. for 3 hours, and then cooled to room temperature, followed by extraction three times with an aqueous solution of 2 M sodium phosphate monobasic. The combined aqueous layer was extracted twice with dichloromethane, and then combined with the organic layer, followed by drying over anhydrous sodium sulfate and concentration in vacuo. The concentrated solution was purified by silica gel column chromatography (hexane:ethyl acetate=4:1) to give a yellow oil of methyl 2-methyl-2-(4-oxocyclohex-2-enyl) propanate (290 mg, 1.48 mmol, 35.5%).

¹H-NMR (CDCl3, Varian 400 MHz): δ1.21 (3H, s), 1.30 (3H, s), 1.72-1.83 (1H, m), 1.99-2.02 (1H, m), 2.38 (1H, td, J=15.4, 4.8 Hz), 2.50-2.58 (1H, m), 2.78-2.86 (1H, m), 3.72 (3H, s), 6.05 (1H, dd, J=10.4, 1.6 Hz), 6.82 (1H, d, J=10.4 Hz).

4-4: Synthesis of methyl 2-methyl-2-(4-oxocyclohexyl) propanate

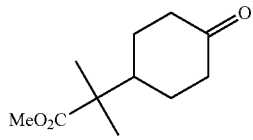

A mixture of methyl 2-methyl-2-(4-oxocyclohex-2-enyl)propanate (290 mg, 1.48 mmol), 10% Pd/C (30 mg) and tetrahydrofuran (15 ml) was stirred at room temperature overnight under a hydrogen atmosphere (1 atm). The reacted solution was filtered through celite, and washed with ethyl acetate. The filtered solution was concentrated in vacuo, and the concentrated solution was purified by silica gel column chromatography (hexane:ethyl acetate=4:1) to give a white solid of methyl 2-methyl-2-(4-oxocyclohexyl)propanate (269 mg, 1.36 mmol, 92%).

¹H-NMR (CDCl3, Varian 400 MHz): δ1.15 (6H, s), 1.42-1.56 (2H, m), 1.86-1.92 (2H, m), 2.04-2.10 (1H, m), 2.28-2.42 (4H, m), 3.67 (3H, s).

4-5: Synthesis of (E)-methyl 2-(4-chloro-3-formyl-5-(hydroxymethylene)cyclohex-3-enyl)-2-methylpropanate

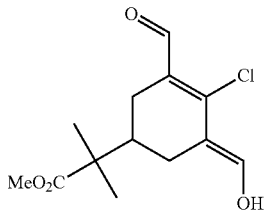 [SMILES: COC(=O)C(C)(C)C1CC(C=O)=C(Cl)/C(=C/O)C1]

Phosphoryl trichloride (0.506 ml, 5.43 mmol) was slowly added dropwise to anhydrous dimethylformamide (0.525 ml, 6.78 mmol) cooled to 0° C. After the reacted solution was stirred at room temperature for 30 minutes, a solution of methyl 2-methyl-2-(4-oxocyclohexyl) propanate (269 mg, 1.36 mmol) diluted in dimethylformamide (6.8 ml) was added dropwise to the reacted solution. The reaction solution was stirred at 55° C. for 2 hours, and then an ice-water mixture was added thereto. After the mixed solution was stirred at room temperature for 24 hours, the generated precipitate was filtered, and then washed with water. The obtained solid was dried in vacuo to give a yellow solid of (E)-methyl 2-(4-chloro-3-formyl-5-(hydroxymethylene)cyclohex-3-enyl)-2-methylpropanate (292 mg, 1.07 mmol, 79%).

¹H-NMR (DMSO-d6, Varian 400 MHz): δ1.14 (6H, s), 1.67-1.86 (3H. m), 2.61 (2H, d, J=15.2 Hz), 3.61 (3H, s), 11.01 (1H, d, J=12.4 Hz).

4-6: Synthesis of (E)-N-(((E)-2-chloro-5-(1-methoxy-2-methyl-1-oxopropan-2-yl)-3-((phenylamino)methylene)cyclohex-1-enyl)methylene)benzenaminium chloride After a solution of (E)-methyl 2-(4-chloro-3-formyl-5-(hydroxymethylene)cyclohex-3-enyl)-2-methylpropanate (292 mg, 1.07 mmol) dissolved in ethanol and dimethylformamide (1.3 ml) was cooled to 0° C., concentrated hydrochloric acid (0.791 ml, 9.11 mmol) was added dropwise thereto. After aniline (0.215 ml, 2.36 mmol) was added dropwise to the reacted solution at 0° C., this reacted solution was stirred at 0° C. for 30 minutes. The reacted solution was added to an ice-water mixture, and then the generated solid was filtered, and washed with water and diisopropyl ether. The filtered solid was dried in vacuo to give a violet solid of (E)-N-(((E)-2-chloro-5-(1-methoxy-2-methyl-1-oxopropan-2-yl)-3-((phenylamino)methylene)cyclohex-1-enyl)methylene)benzenaminium chloride (483 mg, 1.05 mmol, 98%).

¹H-NMR (DMSO-d6, Varian 400 MHz): δ1.31 (6H, s), 2.00-2.05 (1H, m), 2.24 (2H, t, J=13.8 Hz), 2.97 (2H, d, J=14.4 Hz), 3.69 (3H, s), 7.27-7.35 (2H, m), 7.46-7.50 (4H, m), 7.57-7.59 (4H, m), 8.53 (2H, brs).

4-7: Synthesis of 2-((E)-2-((E)-2-chloro-3-((E)-2-(3-ethyl-1,1-dimethyl-7-sulfo-1H-benzo[e]indol-2(3H)-ylidene)ethylidene)-5-(1-methoxy-2-methyl-1-oxopropan-2-yl)cyclohex-1-enyl)vinyl)-3-ethyl-1,1-dimethyl-1H-benzo[e]indolium-7-sulfonate

53

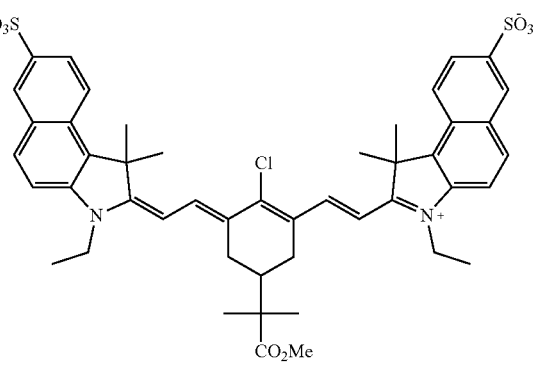

After a solution of sodium acetate (54 mg, 0.653 mmol) was added to a solution of (E)-N-(((E)-2-chloro-5-(1-methoxy-2-methyl-1-oxopropan-2-yl)-3-((phenylamino)

methylene)cyclohex-1-enyl)methylene)benzenaminium chloride (100 mg, 0.218 mmol) and 3-ethyl-1,1,2-trimethyl-1H-benzo[e]indolium-7-sulfonate (276 mg, 0.871 mmol), dissolved in ethanol (4.4 ml), the mixture was refluxed for 3 hours. The reacted solution was concentrated in vacuo, and then the concentrated solution was purified by silica gel column chromatography (dichloromethane:methanol:acetic acid=95:5:0.05) to give a dark blue solid of 2-((E)-2-((E)-2-chloro-3-((E)-2-(3-ethyl-1,1-dimethyl-7-sulfo-1H-benzo[e]indol-2(3H)-ylidene)ethylidene)-5-(1-methoxy-2-methyl-1-oxopropan-2-yl)cyclohex-1-enyl)vinyl)-3-ethyl-1,1-dimethyl-1H-benzo[e]indolium-7-sulfonate (43.8 mg, 0.044 mmol, 20.2%).

$^1$H-NMR (DMSO-d6, Varian 400 MHz): δ1.33 (6H, s), 1.39 (6H, t, J=7.0 Hz), 1.95 (12H, s), 2.05-2.09 (1H, m), 2.32 (2H, t, J=14.0 Hz), 2.83 (2H, d, J=13.2 Hz), 3.70 (3H, s), 4.35-4.42 (4H, m), 6.32 (2H, d, J=14.4 Hz), 7.79 (2H, d, J=8.8 Hz), 7.85 (2H, d, J=8.8 Hz), 8.18 (2H, d, J=8.8 Hz), 8.27-8.29 (4H, m), 8.38 (2H, d, J=14.0 Hz).

Example 5

7-bromo-2-((E)-2-((E)-3-((E)-2-(7-bromo-3-ethyl-1,1-dimethyl-1H-benzo[e]indol-2(3H)-ylidene)ethylidene)-2-chloro-5-(1-methoxy-2-methyl-1-oxopropan-2-yl)cyclohex-1-enyl)vinyl)-3-ethyl-1,1-dimethyl-1H-benzo[e]indolium iodide—See Synthesis Scheme 3

[Compound E]

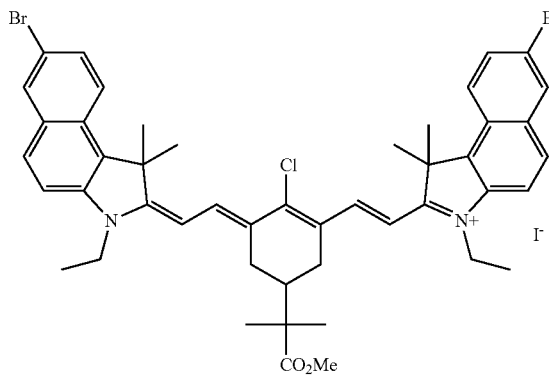

54

After a solution of sodium acetate (54 mg, 0.653 mmol) was added to a solution of (E)-N-(((E)-2-chloro-5-(1-methoxy-2-methyl-1-oxopropan-2-yl)-3-((phenylamino)methylene)cyclohex-1-enyl)methylene)benzenaminium chloride (100 mg, 0.218 mmol) and 7-bromo-3-ethyl-1,1,2-trimethyl-1H-benzo[e]indolium iodide (213 mg, 0.479 mmol), dissolved in ethanol (4.35 ml), the mixture was refluxed for 3 hours. The reacted solution was concentrated in vacuo, and then the concentrated solution was purified by silica gel column chromatography (dichloromethane:methanol=95:5) to give a dark blue solid of 7-bromo-2-((E)-2-((E)-3-((E)-2-(7-bromo-3-ethyl-1,1-dimethyl-1H-benzo[e]indol-2(3H)-ylidene)ethylidene)-2-chloro-5-(1-methoxy-2-methyl-1-oxopropan-2-yl)cyclohex-1-enyl)vinyl)-3-ethyl-1,1-dimethyl-1H-benzo[e]indolium iodide (102 mg, 0.102 mmol, 46.9%).

$^1$H-NMR (DMSO-d6, Varian 400 MHz): δ1.33 (6H, s), 1.37 (6H, t, J=7.2 Hz), 1.94 (12H, s), 2.04 (1H, t, J=12.2 Hz), 2.32 (2H, t, J=14.0 Hz), 2.83 (2H, d, J=13.2 Hz), 3.70 (3H, s), 4.35-4.48 (4H, m), 6.34 (2H, d, J=14.4 Hz), 7.76 (2H, d, J=8.8 Hz), 7.86 (2H, d, J=8.8 Hz), 8.12 (2H, d, J=9.2 Hz), 8.28 (2H, d, J=9.2 Hz), 8.36-8.39 (4H, m).

Example 6

2-((E)-2-((E)-2-chloro-3-((E)-2-(3-ethyl-7-methoxy-1,1-dimethyl-1H-benzo[e]indol-2(3H)-ylidene)ethylidene)-5-(1-methoxy-2-methyl-1-oxopropan-2-yl)cyclohex-1-enyl) vinyl)-3-ethyl-7-methoxy-1,1-dimethyl-1H-benzo[e]indolium iodide—See Synthesis Scheme 3

[Compound F]

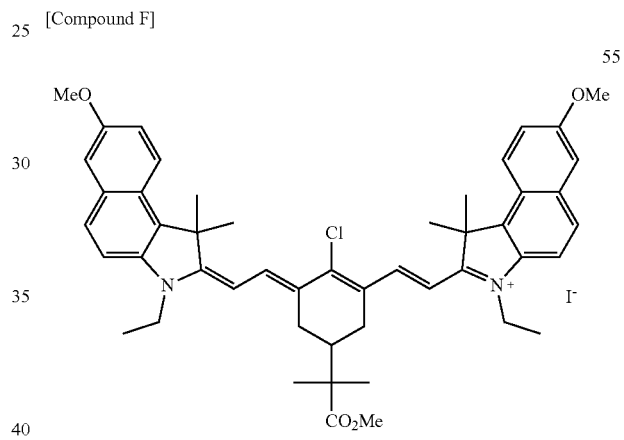

55

After a solution of sodium acetate (268 mg, 3.27 mmol) was added to a solution of (E)-N-(((E)-2-chloro-5-(1-methoxy-2-methyl-1-oxopropan-2-yl)-3-((phenylamino)methylene)cyclohex-1-enyl)methylene)benzenaminium chloride (0.1 g, 0.218 mmol) and 3-ethyl-7-methoxy-1,1,2-trimethyl-1H-benzo[e]indolium iodide (946 mg, 2.394 mmol), dissolved in ethanol (22 ml), the mixture was refluxed for 3 hours. The reacted solution was concentrated in vacuo, and then the concentrated solution was purified by silica gel column chromatography (dichloromethane:methanol=95:5) to give a dark blue solid of 2-((E)-2-((E)-2-chloro-3-((E)-2-(3-ethyl-7-methoxy-1,1-dimethyl-1H-benzo[e]indol-2(3H)-ylidene)ethylidene)-5-(1-methoxy-2-methyl-1-oxopropan-2-yl)cyclohex-1-enyl)vinyl)-3-ethyl-7-methoxy-1,1-dimethyl-1H-benzo[e]indolium iodide (859 mg, 0.956 mmol, 88%).

$^1$H-NMR (DMSO-d6, Varian 400 MHz): δ1.33 (6H, s), 1.37 (6H, t, J=7.0 Hz), 1.93 (12H, s), 2.00-2.07 (1H, m), 2.30 (2H, t, J=13.8 Hz), 2.81 (2H, d, J=13.2 Hz), 3.70 (3H, s), 3.91 (6H, s), 4.35-4.40 (4H, m), 6.28 (2H, d, J=14.4 Hz), 7.33 (2H, dd, J=8.8, 1.6 Hz), 7.52 (2H, s), 7.75 (2H, d, J=11.2 Hz), 8.01 (2H, d, J=8.8 Hz), 8.24 (2H, d, J=9.6 Hz), 8.33 (2H, d, J=10.4 Hz).

Example 7

2-((E)-2-((E)-2-(4-carboxyphenylthio)-3-((E)-2-(3-ethyl-1,1-dimethyl-7-sulfo-1H-benzo[e]indol-2(3H)-ylidene)ethylidene)-5-(1-methoxy-2-methyl-1-oxopropan-2-yl)cyclohex-1-enyl)vinyl)-3-ethyl-1,1-dimethyl-1H-benzo[e]indolium-7-sulfonate—See Synthesis Scheme 4

[Compound G]

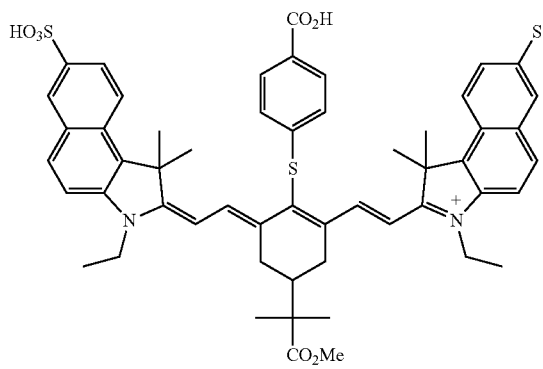

After 4-mercaptobenzoic acid (28.3 mg, 0.184 mmol) was added to a solution of 2-((E)-2-((E)-2-chloro-3-((E)-2-(3-ethyl-1,1-dimethyl-7-sulfo-1H-benzo[e]indol-2(3H)-ylidene)ethylidene)-5-(1-methoxy-2-methyl-1-oxopropan-2-yl)cyclohex-1-enyl)vinyl)-3-ethyl-1,1-dimethyl-1H-benzo[e]indolium-7-sulfonate (100 mg, 0.115 mmol) dissolved in dimethylformamide (1.2 ml), this mixture was stirred at room temperature overnight. The reacted solution was concentrated in vacuo, and then ethanol was added to the obtained solid, followed by stirring at room temperature. The solid was filtered, and washed with ethanol to give a dark blue solid of 2-((E)-2-((E)-2-(4-carboxyphenylthio)-3-((E)-2-(3-ethyl-1,1-dimethyl-7-sulfo-1H-benzo[e]indol-2(3H)-ylidene)ethylidene)-5-(1-methoxy-2-methyl-1-oxopropan-2-yl)cyclohex-1-enyl)vinyl)-3-ethyl-1,1-dimethyl-1H-benzo[e]indolium-7-sulfonate (92 mg, 0.093 mmol, 81%).

$^1$H-NMR (DMSO-d6, Varian 400 MHz): δ1.34-1.38 (12H, m), 1.66, 1.75 (12H, s, s), 2.10-2.20 (1H, m), 2.38 (2H, t, J=13.6 Hz), 2.90 (2H, d, J=13.2 Hz), 3.73 (3H, s), 4.30-4.40 (4H, m), 6.34 (2H, d, J=14.8 Hz), 7.46 (2H, d, J=8.4 Hz), 7.74 (2H, d, J=8.8 Hz), 7.80 (2H, d, J=8.8 Hz), 7.92 (2H, d, J=8.4 Hz), 8.14 (2H, d, J=8.8 Hz), 8.19 (2H, d, J=8.8 Hz), 8.24 (2H, s), 8.68 (2H, d, J=14.0 Hz).

Example 8

4-((E)-6-((E)-2-(3-ethyl-7-methoxy-1,1-dimethyl-1H-benzo[e]indol-2(3H)-ylidene)ethylidene)-2-((E)-2-(3-ethyl-7-methoxy-1,1-dimethyl-1H-benzo[e]indolium-2-yl) vinyl)-4-(1-methoxy-2-methyl-1-oxopropan-2-yl)cyclohex-1-enylthio)benzoate—See Synthesis Scheme 4

[Compound H]

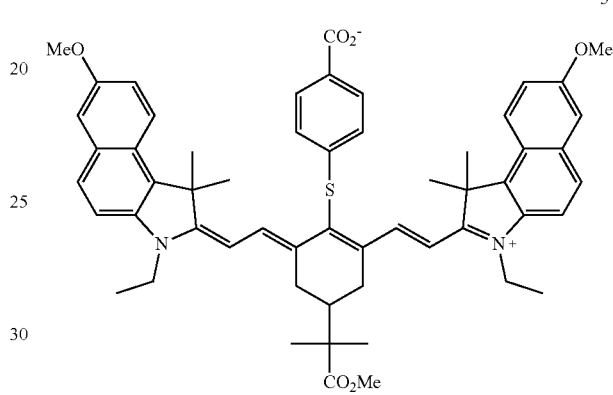

After 4-mercaptobenzoic acid (51.4 mg, 0.334 mmol) was added to a solution of 2-((E)-2-((E)-2-chloro-3-((E)-2-(3-ethyl-7-methoxy-1,1-dimethyl-1H-benzo[e]indol-2(3H)-ylidene)ethylidene)-5-(1-methoxy-2-methyl-1-oxopropan-2-yl)cyclohex-1-enyl)vinyl)-3-ethyl-7-methoxy-1,1-dimethyl-1H-benzo[e]indolium iodide (100 mg, 0.111 mmol) dissolved in dimethylformamide (0.6 ml), this mixture was stirred at room temperature overnight. The reacted solution was concentrated in vacuo, and then the concentrated solution was purified by silica gel column chromatography (dichloromethane:methanol=97:3) to give a dark blue solid of 4-((E)-6-((E)-2-(3-ethyl-7-methoxy-1,1-dimethyl-1H-benzo[e]indol-2(3H)-ylidene)ethylidene)-2-((E)-2-(3-ethyl-7-methoxy-1,1-dimethyl-1H-benzo[e]indolium-2-yl)vinyl)-4-(1-methoxy-2-methyl-1-oxopropan-2-yl)cyclohex-1-enylthio)benzoate (85.3 mg, 0.096 mmol, 86%).

$^1$H-NMR (DMSO-d6, Varian 400 MHz): δ1.30 (6H, t, J=7.2 Hz), 1.33 (6H, s), 1.59, 1.68 (12H, s, s), 2.05-2.11 (1H, m), 2.32 (2H, t, J=13.8 Hz), 2.84 (2H, d, J=13.6 Hz), 3.69 (3H, s), 3.85 (6H, s), 4.25-4.35 (4H, m), 6.26 (2H, d, J=14.4 Hz), 7.23 (2H, dd, J=9.2, 2.4 Hz), 7.40 (2H, d, J=8.4 Hz), 7.45 (2H, d, J=2.4 Hz), 7.66 (2H, d, J=8.8 Hz), 7.86 (2H, d, J=8.4 Hz), 7.93 (2H, d, J=8.8 Hz), 8.12 (2H, d, J=9.2 Hz), 8.60 (2H, d, J=14.8 Hz).

Example 9

2-((E)-2-((E)-2-(4-(2-aminoethylcarbamoyl)phenyl-thio)-3-((E)-2-(3-ethyl-7-methoxy-1,1-dimethyl-1H-benzo[e]indol-2(3H)-ylidene)ethylidene)-5-(1-methoxy-2-methyl-1-oxopropan-2-yl)cyclohex-1-enyl)vinyl)-3-ethyl-7-methoxy-1,1-dimethyl-1H-benzo[e]indolium iodide—See Synthesis Scheme 5

[Compound I]

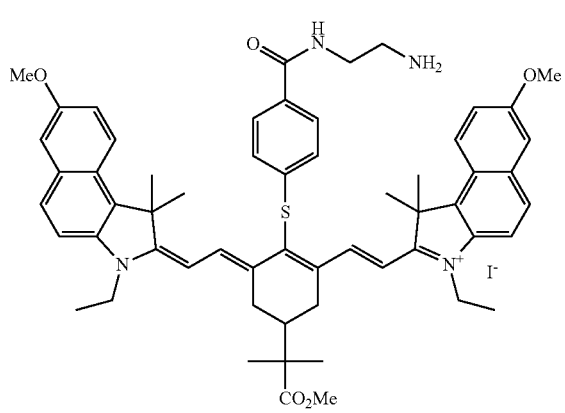

9-1: Synthesis of tert-butyl 2-aminoethyl carbamate

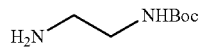

A solution of BOC$_2$O (6.49 ml, 27.9 mmol) dissolved in dichloromethane (400 ml) was added dropwise to a solution of ethylene diamine (11.32 ml, 168 mmol) diluted with dichloromethane (50 ml) at room temperature for 6 hours. The reacted solution was stirred at room temperature for 24 hours, and then concentrated in vacuo. The concentrated solution was diluted in an aqueous solution (300 ml) of 2 M sodium carbonate, and then extracted twice with dichloromethane (300 ml). The combined organic layer was dried over magnesium sulfate, and concentrated in vacuo to give a colorless oil of tert-butyl 2-aminoethyl carbamate (4.28 g, 26.7 mmol, 96%).

$^1$H-NMR (CDCl3, Varian 400 MHz): δ1.16 (2H, brs), 1.45 (9H, s), 2.80 (2H, t, J=5.8 Hz), 3.15-3.23 (2H, m), 4.88 (1H, brs).

9-2: Synthesis of 4,4'-disulfanediyldibenzoic acid

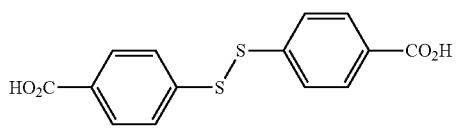

After iodine was dissolved to be saturated in 95% ethanol, the solution was slowly added dropwise at room temperature to a solution of 4-mercapto benzoic acid (500 mg, 3.24 mmol) dissolved in ethanol (32 ml). As the reaction proceeded, the reddish brown color of iodine disappeared and crystals were formed, and the iodine was continuously added until the yellow color of the reacted solution no longer disappeared. The generated soli was filtered, and washed with ethanol. The filtered crystals were dried at 50° C. in vacuo to give a gray solid of 4,4'-disulfanediyldibenzoic acid (413 mg, 1.348 mmol, 41.6%).

$^1$H-NMR (DMSO-d6, Varian 400 MHz): δ7.64 (4H, d, J=7.6 Hz), 7.93 (4H, d, J=8.0 Hz), 13.06 (2H, s).

9-3: Synthesis of tert-butyl N-[2-[[4-[[4-[2-(tert-butoxycarbonylamino)ethyl carbamoyl]phenyl]disulfanyl]benzoyl]amino]ethyl]carbamate

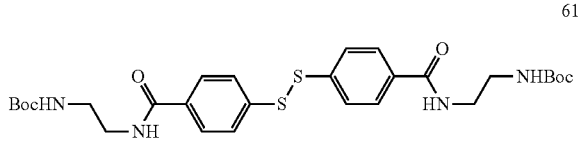 [SMILES: CC(C)(C)OC(=O)NCCNC(=O)c1ccc(SSc2ccc(C(=O)NCCNC(=O)OC(C)(C)C)cc2)cc1]

After 4,4'-disulfanediylbenzoic acid (200 mg, 0.653 mmol) was dissolved in dimethylformamide (6.5 ml), 1-ethyl-3-(3-dimethylaminopropyl) carbodiimide hydrochloride (375 mg, 1.96 mmol), hydroxybenzotriazole (300 mg, 1.96 mmol), and 4-dimethylaminopyridine (7.98 mg, 0.065 mmol) were introduced thereto. The reacted solution was stirred at 0° C. for 30 minutes, and then tert-butyl-2-aminoethyl carbamate (314 mg, 1.96 mmol) was introduced thereto, followed by stirring at room temperature for 3 days. The reacted solution was diluted with ethyl acetate, and then sequentially washed with an aqueous solution of 10% citric acid, an aqueous solution of saturated sodium bicarbonate, and salt water, followed by concentration in vacuo. The obtained solid was washed with ethyl acetate to give a white solid of tert-butyl N-[2-[[4-[[4-[2-(tert-butoxycarbonylamino)ethyl carbamoyl]phenyl]disulfanyl]benzoyl]amino]ethyl]carbamate (349 mg, 0.591 mmol, 90%).

$^1$H-NMR (DMSO-d6, Varian 400 MHz): δ1.35 (18H, s), 3.04-3.10 (4H, m), 3.07 (4H, q, J=6.0 Hz), 3.26 (4H, q, J=5.9 Hz), 6.89 (2H, t, J=5.4 Hz), 7.60 (4H, d, J=8.4 Hz), 7.82 (4H, d, J=8.0 Hz), 8.44-8.53 (2H, m).

9-4: Synthesis of 2-(4-mercaptobenzamido)ethyl carbamate

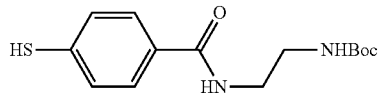

After tert-butyl N-[2-[[4-[[4-[2-(tert-butoxycarbonylamino)ethyl carbamoyl]phenyl]disulfanyl]benzoyl]amino]ethyl]carbamate (200 mg, 0.339 mmol) was dissolved in ethanol (3.4 ml) and tetrahydrofuran (3.4 ml), NaBH$_4$ (51.2 mg, 1.354 mmol) was sub-divisionally introduced thereto at 0° C. The temperature of the reacted solution was raised to room temperature, followed by stirring for 2 hours. After the reacted solution was concentrated in vacuo, water and ethyl acetate were added to the concentrated solution, and then the mixture was acidified to pH 4 using 2 N hydrochloric acid. The separated organic layer was washed with salt water, dried over sodium sulfate, and then concentrated in vacuo, to give a white solid of 2-(4-mercaptobenzamido)ethyl carbamate (218 mg, 0.736 mmol). The obtained compound was used for a next step without separate purification.

$^1$H-NMR (DMSO-d6, Varian 400 MHz): δ1.37 (9H, s), 3.08 (2H, q, J=6.0 Hz), 3.26 (2H, q, J=6.3 Hz), 5.76 (1H, d, J=13.2 Hz), 6.91-6.93 (1H, m), 7.35 (2H, d, J=8.4 Hz), 7.70 (2H, d, J=8.0 Hz), 8.34-8.40 (1H, m).

9-5: Synthesis of N-(2-aminoethyl)-4-mercaptobenzamide hydrochloride

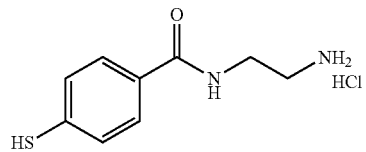

A solution of 4 M HCl/1,4-dioxane (Sigma-Aldrich, 0.843 ml, 3.37 mmol) was added dropwise at 0° C. to a solution of tert-butyl 2-(4-mercaptobenzamido)ethyl carbamate (200 mg, 0.675 mmol) dissolved in dichloromethane (6.8 ml). The reacted solution was stirred at room temperature for 5 hours, and then concentrated in vacuo. After ethyl ether (5 ml) was added to a residual solid, the solid was filtered, and washed with ethyl ether, to give a gray solid of N-(2-aminoethyl)-4-mercaptobenzamide hydrochloride (138 mg, 0.593 mmol, 88%).

$^1$H-NMR (DMSO-d6, Varian 400 MHz): δ2.87 (2H, q, J=5.9 Hz), 3.49 (2H, q, J=6.0 Hz), 5.85 (1H, s), 7.38 (2H, d, J=8.4 Hz), 7.77 (2H, d, J=8.4 Hz), 7.95 (3H, brs), 8.65 (1H, s).

9-6: Synthesis of 2-((E)-2-((E)-2-(4-(2-aminoethylcarbamoyl)phenylthio)-3-((E)-2-(3-ethyl-7-methoxy-1,1-dimethyl-1H-benzo[e]indol-2(3H)-ylidene)ethylidene)-5-(1-methoxy-2-methyl-1-oxopropan-2-yl)cyclohex-1-enyl)vinyl)-3-ethyl-7-methoxy-1,1-dimethyl-1H-benzo[e]indolium iodide

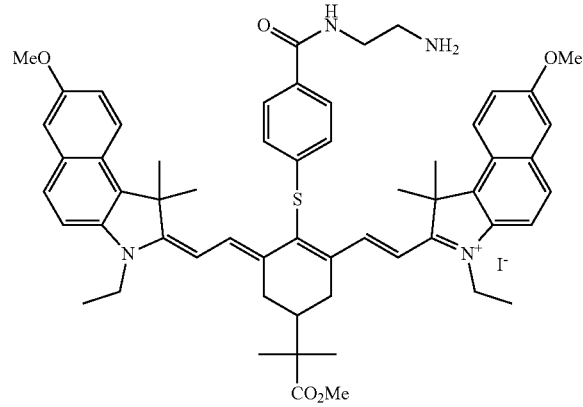 [SMILES: CCN1/C(=C/C=C2\CC(C(C)(C)C(=O)OC)CC(/C=C/C3=[N+](CC)c4ccc5cc(OC)ccc5c4C3(C)C)=C2Sc2ccc(C(=O)NCCN)cc2)C(C)(C)c2c1ccc1cc(OC)ccc21 ; [I-]]

After N-(2-aminoethyl)-4-mercaptobenzamide hydrochloride (62.1 mg, 0.267 mmol) and 4-dimethylamino pyridine (32.6 mg, 0.267 mmol) were added to a solution of 2-((E)-2-((E)-2-chloro-3-((E)-2-(3-ethyl-7-methoxy-1,1-dimethyl-1H-benzo[e]indol-2(3H)-ylidene)ethylidene)-5-(1-methoxy-2-methyl-1-oxopropan-2-yl)cyclohex-1-enyl)vinyl)-3-ethyl-7-methoxy-1,1-dimethyl-1H-benzo[e]indolium iodide (240 mg, 0.267 mmol) dissolved in dimethylformamide (1.3 ml), the mixture was stirred at room temperature for 1 hour. The reacted solution was concentrated in vacuo, and then the concentrated solution was purified by silica gel column chromatography (dichloromethane:methanol=98:2 to 95:5) to give a dark blue solid of 2-((E)-2-((E)-2-(4-(2-aminoethylcarbamoyl)phenylthio)-3-((E)-2-(3-ethyl-7-methoxy-1,1-dimethyl-1H-benzo[e]indol-2(3H)-ylidene)ethylidene)-5-(1-methoxy-2-methyl-1-oxopropan-2-yl)cyclohex-1-enyl)vinyl)-3-ethyl-7-methoxy-1,1-dimethyl-1H-benzo[e]indolium iodide (247 mg, 0.233 mmol, 87%).

$^1$H-NMR (DMSO-d6, Varian 400 MHz): δ1.32-1.37 (12H, m), 1.65, 1.72 (12H, s, s), 2.01-2.13 (2H, m), 2.35 (3H, t, J=13.6 Hz), 2.61 (2H, t, J=6.4 Hz), 2.86 (2H, d, J=13.6 Hz), 3.17-2.21 (2H, m), 3.72 (3H, s), 3.89 (6H, s), 4.30-4.40 (4H, m), 6.29 (2H, d, J=14.4 Hz), 7.27 (2H, dd, J=9.2, 2.4 Hz), 7.41 (2H, d, J=8.4 Hz), 7.49 (2H, d, J=2.4 Hz), 7.70 (2H, d, J=8.8 Hz), 7.81 (2H, d, J=8.4 Hz), 7.97 (2H, d, J=9.2 Hz), 8.16 (2H, d, J=9.6 Hz), 8.33 (1H, t, J=5.2 Hz), 8.66 (2H, d, J=14.4 Hz).

Example 10

3-ethyl-2-((E)-2-((E)-3-((E)-2-(3-ethyl-7-methoxy-1,1-dimethyl-1H-benzo[e]indol-2(3H)-ylidene)ethylidene)-2-(4-(2-isothiocyantoethylcarbamoyl)phenylthio)-5-(1-methoxy-2-methyl-1-oxopropan-2-yl)cyclohex-1-enyl) vinyl)-7-methoxy-1,1-dimethyl-1H-benzo[e]indolium iodide—See Synthesis Scheme 6

[Compound J]

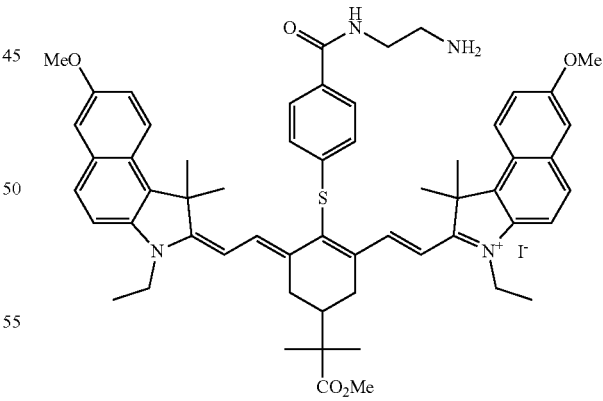

After di(1H-imidazol-1-yl)methanethione (18 mg, 0.099 mmol) was introduced at room temperature to a solution of 2-((E)-2-((E)-2-(4-(2-aminoethylcarbamoyl)phenylthio)-3-((E)-2-(3-ethyl-7-methoxy-1,1-dimethyl-1H-benzo[e]indol-2(3H)-ylidene)ethylidene)-5-(1-methoxy-2-methyl-1-oxopropan-2-yl)cyclohex-1-enyl)vinyl)-3-ethyl-7-methoxy-1,1-dimethyl-1H-benzo[e]indolium iodide (46 mg, 0.049 mmol) dissolved in dimethylformamide (1 mL), this mixture was stirred at room temperature for 30 minutes. The reacted solution was concentrated in vacuo, and then the concentrated solution was purified by silica gel column chromatography (dichloromethane:methanol=97:3 to 95:5) to give a dark blue solid of 3-ethyl-2-((E)-2-((E)-3-((E)-2-(3-ethyl-7-methoxy-1,1-dimethyl-1H-benzo[e]indol-2(3H)-ylidene)ethylidene)-2-(4-(2-isothiocyantoethylcarbamoyl)phenylthio)-5-(1-methoxy-2-methyl-1-oxopropan-2-yl) cyclohex-1-enyl)vinyl)-7-methoxy-1,1-dimethyl-1H-benzo[e]indolium iodide (24.6 mg, 0.022 mmol, 45.3%).

¹H-NMR (DMSO-d6, Varian 400 MHz): δ1.34 (6H, t, J=7.2 Hz), 1.37 (6H, s), 1.64, 1.72 (12H, s, s), 2.08-2.16 (1H, m), 2.36 (2H, t, J=14.4 Hz), 2.92 (2H, d, J=18.8 Hz), 3.43-3.48 (2H, m), 3.72 (3H, s), 3.70-3.77 (2H, m), 3.89 (6H, s), 4.28-4.38 (4H, m), 6.29 (2H, d, J=14.4 Hz), 7.27 (2H, dd, J=9.2, 2.4 Hz), 7.44 (2H, d, J=8.0 Hz), 7.48 (2H, d, J=2.4 Hz), 7.69 (2H, d, J=9.2 Hz), 7.82 (2H, d, J=8.8 Hz), 7.97 (2H, d, J=8.8 Hz), 8.14 (2H, d, J=9.6 Hz), 8.63-8.68 (3H, m).

Example 11

2-((E)-2-((E)-2-(4-(2-aminoethylcarbamoyl)phenylthio)-3-((E)-2-(3-ethyl-7-methoxy-1,1-dimethyl-1H-benzo[e]indol-2(3H)-ylidene)ethylidene)cyclohex-1-enyl)vinyl)-3-ethyl-7-methoxy-1,1-dimethyl-1H-benzo[e]indolium iodide

[Compound K]

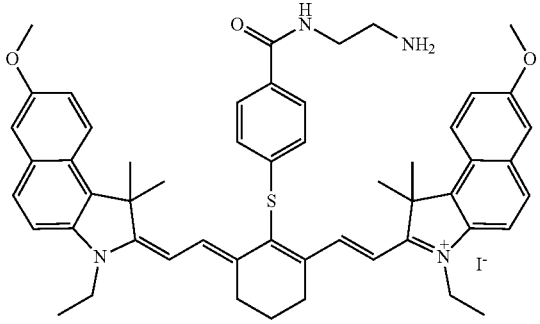

66

11-1: Synthesis of (E)-2-chloro-3-(hydroxymethylene) cyclohex-1-enecarbaldehyde

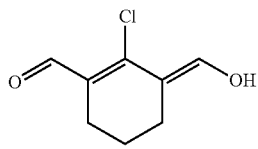 [SMILES: O=CC1=C(Cl)/C(=C/O)CCC1]

After dimethylformamide (11.8 ml, 153 mmol) was slowly added dropwise to phosphoryl trichloride (11.4 ml, 122 mmol) cooled to 0° C., the reacted solution was stirred at room temperature for 30 minutes. After cyclohexanone (3 g, 30.6 mmol) diluted in dimethylformamide (61 ml) was added dropwise to the reacted solution, the mixture was stirred at 55° C. for 2 hours. The reacted solution was cooled to room temperature, and then an ice-water mixture was added thereto, followed by stirring for 24 hours. The generated solid was filtered and washed with water and diisopropylether, to give a yellow solid of (E)-2-chloro-3-(hydroxymethylene)cyclohex-1-enecarbaldehyde (3.07 g, 17.8 mmol, 58.2%).

¹H-NMR (CDCl3, Varian 400 MHz): δ1.55-1.62 (2H, m), 2.20-2.50 (4H, m), 3.35 (1H, s), 7.53 (1H, s), 10.09 (1H, s), 10.85 (1H, s).

11-2: Synthesis of (E)-N-(((E)-2-chloro-3-((phenylamino)methylene)cyclohex-1-enyl)methylene)benzenaminium chloride

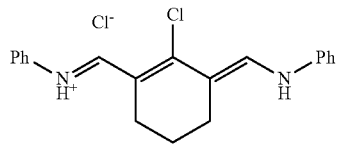

68

After a solution of (E)-2-chloro-3-(hydroxymethylene)cyclohex-1-enecarbaldehyde (3.07 g, 17.8 mmol) in ethanol (35.6 ml) and dimethylformamide (23.7 ml) was cooled to 0° C., concentrated hydrochloric acid (13.1 ml, 151 mmol) was added dropwise thereto. After aniline (4.87 ml, 53.4 mmol) was added dropwise to the reacted solution at 0° C., this reacted solution was stirred at 0° C. for 30 minutes. The reacted solution was added to an ice-water mixture, and then the generated solid was filtered, and washed with water and diisopropyl ether. The filtered solid was dried in vacuo to give a violet solid of (E)-N-(((E)-2-chloro-3-((phenylamino)methylene)cyclohex-1-enyl)methylene)benzenaminum chloride (6.69 g, 18.6 mmol). The obtained solid was used for a next step without separate purification.

¹H-NMR (DMSO-d6, Varian 400 MHz): δ1.82-1.90 (2H, m), 2.72-2.78 (4H, m), 7.25-7.92 (3H, m), 7.47 (4H, t, J=8.0 Hz), 7.60 (4H, d, J=8.0 Hz), 8.56 (2H, s).

11-3: Synthesis of 2-((E)-2-((E)-2-chloro-3-((E)-2-(3-ethyl-7-methoxy-1,1-dimethyl-1H-benzo[e]indol-2(3H)-ylidene)ethylidene)cyclohex-1-enyl)vinyl)-3-ethyl-7-methoxy-1,1-dimethyl-1H-benzo[e]indolium iodide

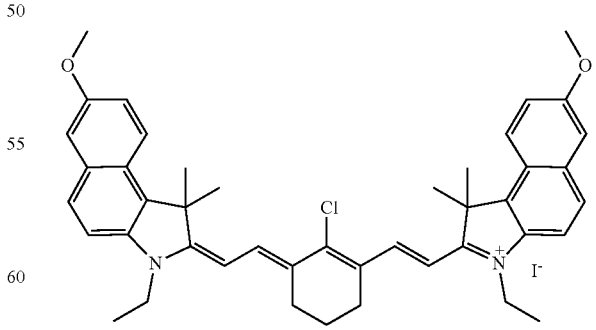

After a solution of sodium acetate (68.5 mg, 0.835 mmol) was added to a solution of (E)-N-(((E)-2-chloro-3-((phenylamino)methylene)cyclohex-1-enyl)methylene)benzeneaminium chloride (100 mg, 0.278 mmol) and 3-ethyl-7- methoxy-1,1,2-trimethyl-1H-benzo[e]indolium iodide (242 mg, 0.612 mmol), dissolved in ethanol (5.6 ml), the mixture was refluxed for 3 hours. The reacted solution was concentrated in vacuo, and then the concentrated solution was purified by silica gel column chromatography (dichloromethane:methanol=20:1 in 100% dichloromethane) to give a dark blue solid of 2-((E)-2-((E)-2-chloro-3-((E)-2-(3-ethyl-7-methoxy-1,1-dimethyl-1H-benzo[e]indol-2(3H)-ylidene)ethylidene)cyclohex-1-enyl) vinyl)-3-ethyl-7-methoxy-1,1-dimethyl-1H-benzo[e]indolium iodide (240 mg, 0.300 mmol). The obtained compound was used for a next step without additional purification.

$^1$H-NMR (DMSO-d6, Varian 400 MHz): δ1.36 (6H, t, J=7.0 Hz), 1.85-1.93 (2H, m), 1.93 (12H, s), 2.72-2.78 (4H, m), 3.91 (6H, s), 4.32-4.40 (4H, m), 6.33 (2H, d, J=14.0 Hz), 7.32 (2H, dd, J=9.2, 2.8 Hz), 7.52 (2H, d, J=2.8 Hz), 7.73 (2H, d, J=9.2 Hz), 8.00 (2H, d, J=8.8 Hz), 8.23 (2H, d, J=8.8 Hz), 8.34 (2H, d, J=14.8 Hz)

11-4: Synthesis of 2-((E)-2-((E)-2-(4-(2-aminoethylcarbamoyl)phenylthio)-3-((E)-2-(3-ethyl-7-methoxy-1,1-dimethyl-1H-benzo[e]indol-2(3H)-ylidene)ethylidene)cyclohex-1-enyl)vinyl)-3-ethyl-7-methoxy-1,1-dimethyl-1H-benzo[e]indolium iodide

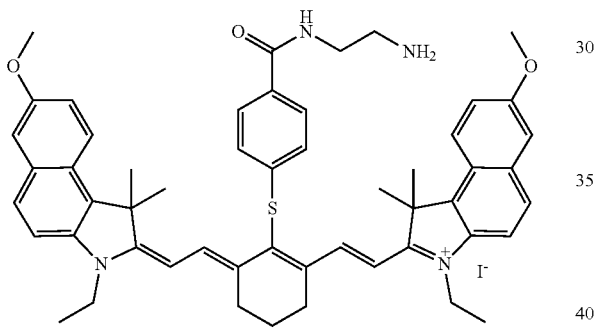

After N-(2-aminoethyl)-4-mercaptobenzamide hydrochloride (69.9 mg, 0.300 mmol) and 4-dimethylamino pyridine (32.7 mg, 0.3 mmol) were added to a solution of 2-((E)-2-((E)-2-chloro-3-((E)-2-(3-ethyl-7-methoxy-1,1-dimethyl-1H-benzo[e]indol-2(3H)-ylidene)ethylidene)cyclohex-1-enyl)vinyl)-3-ethyl-7-methoxy-1,1-dimethyl-1H-benzo[e]indolium iodide (240 mg, 0.300 mmol) dissolved in dimethylformamide (6 ml), the mixture was stirred at room temperature for 1 hour. The reacted solution was concentrated in vacuo, and then the concentrated solution was purified by amino silica gel column chromatography (dichloromethane:methanol=20:1 in 100% dichloromethane) to give a dark blue solid of 2-((E)-2-((E)-2-(4-(2-aminoethylcarbamoyl)phenylthio)-3-((E)-2-(3-ethyl-7-methoxy-1,1-dimethyl-1H-benzo[e]indol-2(3H)-ylidene)ethylidene)cyclohex-1-enyl)vinyl)-3-ethyl-7-methoxy-1,1-dimethyl-1H-benzo [e]indolium iodide (122 mg, 0.147 mmol, 48.8%).

$^1$H-NMR (DMSO-d6, Varian 400 MHz): δ1.33 (6H, t, J=7.0 Hz), 1.69 (12H, s), 1.93-2.00 (2H, m), 2.59 (2H, t, J=6.6 Hz), 2.68-2.75 (4H, m), 3.12-3.20 (2H, m), 3.89 (6H, s), 4.27-4.35 (4H, m), 6.34 (2H, d, J=14.8 Hz), 7.27 (2H, d, J=11.6 Hz), 7.40 (2H, d, J=8.4 Hz), 7.48 (2H, s), 7.68 (2H, d, J=8.8 Hz), 7.81 (2H, d, J=8.4 Hz), 7.96 (2H, d, J=9.2 Hz), 8.15 (2H, d, J=9.2 Hz), 8.30-8.36 (1H, m), 8.67 (2H, d, J=14.4 Hz).

Example 12

2-((E)-2-((E)-2-(4-(2-aminoethylcarbamoyl)phenylthio)-5-tert-butyl-3-((E)-2-(3-ethyl-7-methoxy-1,1-dimethyl-1H-benzo[e]indol-2(3H)-ylidene)ethylidene)cyclohex-1-enyl)vinyl)-3-ethyl-7-methoxy-1,1-dimethyl-1H-benzo[e]indolium iodide

[Compound L]

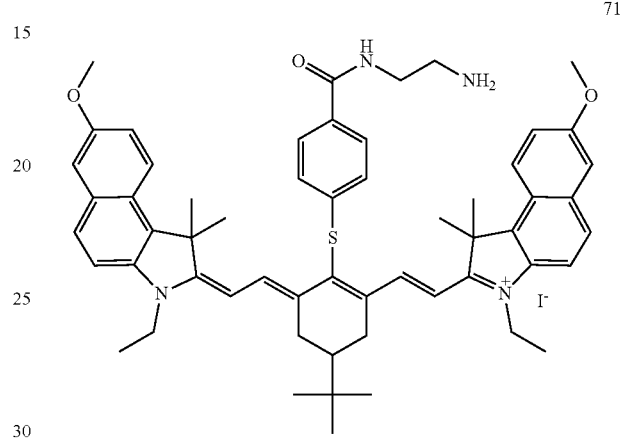

12-1: Synthesis of (E)-5-tert-butyl-2-chloro-3-(hydroxymethylene) cyclohex-1-enecarbaldehyde

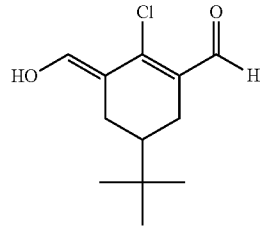

After dimethylformamide (5.02 ml, 64.8 mmol) was slowly added dropwise to phosphoryl trichloride (4.83 ml, 51.9 mmol) cooled to 0° C., the reacted solution was stirred at room temperature for 30 minutes. After 4-tert-butyl cyclohexanone (2 g, 12.97 mmol) diluted in dimethylformamide (30 ml) was added dropwise to the reacted solution, the mixture was stirred at 55° C. for 2 hours. The reacted solution was cooled to room temperature, and then an ice-water mixture was added thereto, followed by stirring for 24 hours. The generated solid was filtered, and then washed with water and diisopropylether, to give a yellow solid of (E)-5-tert-butyl-2-chloro-3-(hydroxymethylene)cyclohex-1-enecarbaldehyde (2.71 g, 11.85 mmol, 91%).

$^1$H-NMR (DMSO-d6, Varian 400 MHz): δ0.90 (9H, s), 1.21 (1H, tt, J=12.2, 3.8 Hz), 1.76 (2H, dd, J=15.6, 12.4 Hz), 2.75 (2H, d, J=14.8 Hz), 10.86 (1H, s)

12-2: Synthesis of (E)-N-(((E)-5-tert-butyl-2-chloro-3-((phenylamino)methylene)cyclohex-1-enyl)methylene)benzenaminium chloride

73

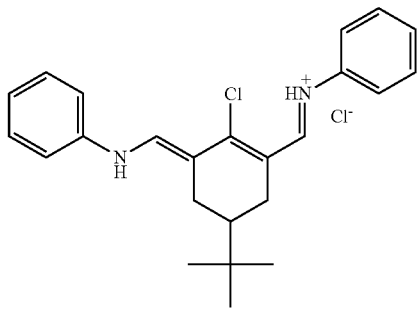

After a solution of (E)-5-tert-butyl-2-chloro-3-(hydroxymethylene)cyclohex-1-enecarbaldehyde (2.7 g, 11.8 mmol) in ethanol (23.6 ml) and dimethylformamide (15.7 ml) was cooled to 0° C., concentrated hydrochloric acid (13.1 ml, 151 mmol) was added dropwise thereto. After aniline (3.23 ml, 35.4 mmol) was added dropwise to the reacted solution at 0° C., this reacted solution was stirred at 0° C. for 30 minutes. The reacted solution was added to an ice-water mixture, and then the generated solid was filtered, and washed with water and diisopropyl ether. The filtered solid was dried in vacuo to give a violet solid of (E)-N-(((E)-5-tert-butyl-2-chloro-3-((phenylamino)methylene)cyclohex-1-enyl)methylene)benzenaminium chloride (3.0 g, 7.22 mmol, 61.2%).

$^1$H-NMR (DMSO-d6, Varian 400 MHz): δ1.07 (9H, s), 1.49 (2H, t, J=12.8 Hz), 2.16 (2H, t, J=14.0 Hz), 3.05 (2H, d, J=15.2 Hz), 7.28 (2H, t, J=7.2 Hz), 7.48 (4H, t, J=7.8 Hz), 7.52-7.60 (4H, m), 8.52 (2H, brs), 11.23 (1H, brs).

12-3: Synthesis of 2-((E)-2-((E)-5-tert-butyl-2-chloro-3-((E)-2-(3-ethyl-7-methoxy-1,1-dimethyl-1H-benzo[e]indol-2(3H)-ylidene)ethylidene)cyclohex-1-enyl) vinyl)-3-ethyl-7-methoxy-1,1-dimethyl-1H-benzo[e]indolium iodide

74

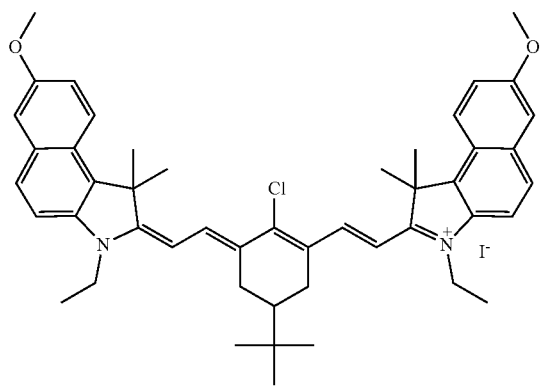

After a solution of sodium acetate (59.2 mg, 0.722 mmol) was added to a solution of (E)-N-(((E)-5-tert-butyl-2-chloro-3-((phenylamino)methylene)cyclohex-1-enyl)methylene)benzenaminium chloride (100 mg, 0.241 mmol) and 3-ethyl-7-methoxy-1,1,2-trimethyl-1H-benzo[e]indolium iodide (209 mg, 0.530 mmol), dissolved in ethanol (4.8 ml), the mixture was refluxed for 3 hours. The reacted solution was concentrated in vacuo, and then the concentrated solution was purified by silica gel column chromatography (dichloromethane:methanol=20:1 in 100% dichloromethane) to give a dark blue solid of 2-((E)-2-((E)-5-tert-butyl-2-chloro-3-((E)-2-(3-ethyl-7-methoxy-1,1-dimethyl-1H-benzo[e]indol-2(3H)-ylidene)ethylidene)cyclohex-1-enyl)vinyl)-3-ethyl-7-methoxy-1,1-dimethyl-1H-benzo[e]indolium iodide (254 mg, 0.297 mmol). The obtained compound was used for a next step without additional purification.

$^1$H-NMR (DMSO-d6, Varian 400 MHz): δ1.09 (9H, s), 1.37 (6H, t, J=7.0 Hz), 1.93 (12H, s), 2.21 (2H, t, J=14.0 Hz), 2.97 (3H, d, J=12.8 Hz), 3.91 (6H, s), 4.35-4.42 (4H, m), 6.34 (2H, d, J=14.0 Hz), 7.32 (2H, dd, J=9.2, 2.8 Hz), 7.52 (2H, d, J=2.4 Hz), 7.73 (2H, d, J=8.8 Hz), 8.00 (2H, d, J=8.8 Hz), 8.23 (2H, d, J=9.6 Hz), 8.34 (2H, d, J=14.8 Hz)

12-4: Synthesis of 2-((E)-2-((E)-2-(4-(2-aminoethylcarbamoyl)phenylthio)-5-tert-butyl-3-((E)-2-(3-ethyl-7-methoxy-1,1-dimethyl-1H-benzo[e]indol-2(3H)-ylidene)ethylidene)cyclohex-1-enyl)vinyl)-3-ethyl-7-methoxy-1,1-dimethyl-1H-benzo[e]indolium iodide

75

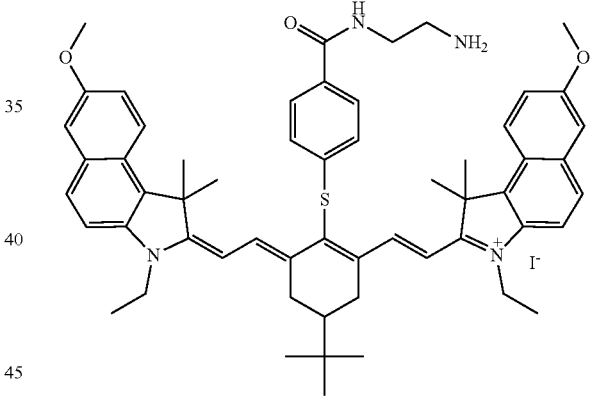

After N-(2-aminoethyl)-4-mercaptobenzamide hydrochloride (69.1 mg, 0.297 mmol) and 4-dimethylamino pyridine (36.3 mg, 0.297 mmol) were added to a solution of 2-((E)-2-((E)-5-tert-butyl-2-chloro-3-((E)-2-(3-ethyl-7-methoxy-1,1-dimethyl-1H-benzo[e]indol-2(3H)-ylidene)ethylidene)cyclohex-1-enyl)vinyl)-3-ethyl-7-methoxy-1,1-dimethyl-1H-benzo[e]indolium iodide (254 mg, 0.297 mmol) dissolved in dimethylformamide (6 ml), the mixture was stirred at room temperature for 1 hour. The reacted solution was concentrated in vacuo, and then the concentrated solution was purified by amino silica gel column chromatography (dichloromethane:methanol=20:1 in 100% dichloromethane) to give a dark blue solid of 2-((E)-2-((E)-2-(4-(2-aminoethylcarbamoyl)phenylthio)-5-tert-butyl-3-((E)-2-(3-ethyl-7-methoxy-1,1-dimethyl-1H-benzo[e]indol-2(3H)-ylidene)ethylidene)cyclohex-1-enyl) vinyl)-3-ethyl-7-methoxy-1,1-dimethyl-1H-benzo[e]indolium iodide (74 mg, 0.083 mmol, 28.1%).

$^1$H-NMR (DMSO-d6, Varian 400 MHz): δ1.13 (9H, s), 1.33 (6H, t, J=7.0 Hz), 1.69, 1.72 (12H, s, s), 2.23-2.32 (2H, m), 3.02 (2H, d, J=13.6 Hz), 3.15-3.20 (2H, m), 3.89 (6H, s), 4.30-4.40 (4H, m), 6.35 (2H, d, J=14.0 Hz), 7.27 (2H, dd, J=9.0, 2.2 Hz), 7.40 (2H, d, J=8.4 Hz), 7.48 (2H, d, J=2.4 Hz), 7.68 (2H, d, J=9.2 Hz), 7.81 (2H, d, J=8.4 Hz), 7.96 (2H, d, J=8.8 Hz), 8.15 (2H, d, J=8.8 Hz), 8.31 (1H, t, J=5.2 Hz), 8.67 (2H, d, J=14.8 Hz).

Preparation Example 1—Preparation of Nano Near-Infrared Contrast Medium

After 2 mg of compound H according to Example 8 was dispersed in 5 ml of an organic solvent, THF, hybridization was induced in a manner in which the dispersion was slowly added dropwise (0.1 mg/sec) to 100 ml of a solution in which 10 mg of a lipid was dissolved, and then homogeneous mixing was induced for 30 minutes or more. Thereafter, after sonication for 10 minutes, the organic solvent was rapidly removed using an evaporator, thereby manufacturing core-shell structured nanoparticles.

Figure 7:
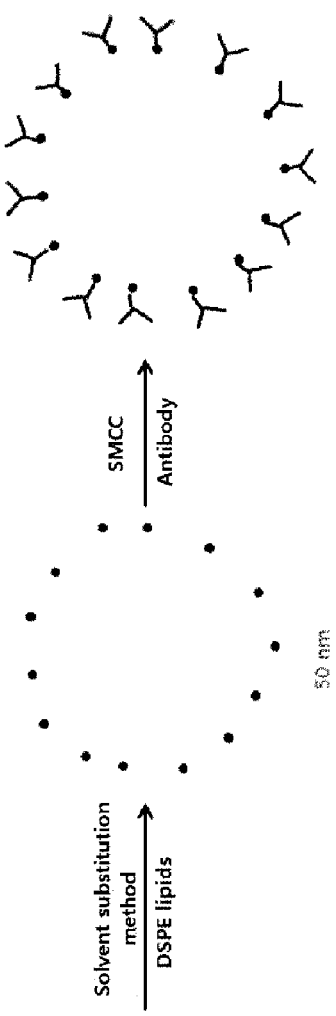
FIG. 7 is a schematic diagram for illustrating a method for preparing a near-infrared fluorescent contrast medium according to an embodiment of the present invention.
Figure 8:
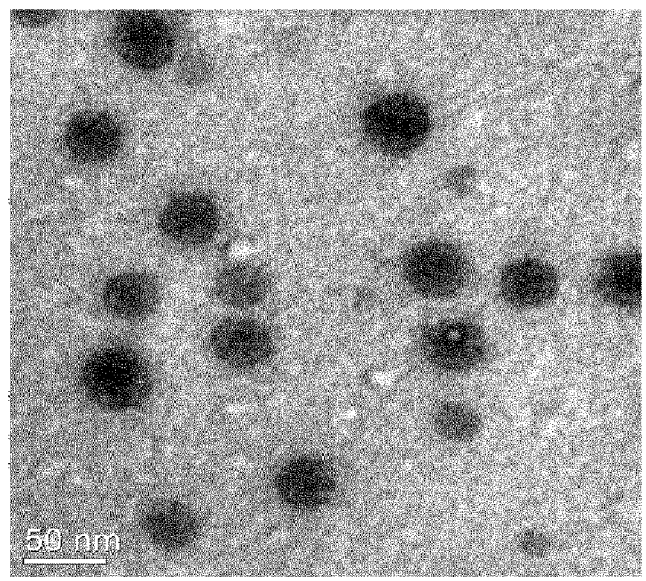
FIG. 8 is a TEM image of core-shell nanoparticles manufactured according to Preparation Example 1.

In the manufactured core-shell structured particles, compound F according to Example 6 is positioned at the core and a lipid is positioned at the shell while a hydrophobic group of the lipid faces toward the core and the hydrophilic group thereof faces outward (see the middle panel of FIG. 7). The core-shell structured particles have a particle diameter of about 50 nm (see FIG. 8).

In order to introduce a maleimide chemical reaction group to the surface of the manufactured core-shell nanoparticles, the core-shell nanoparticles were treated with 6.874 mM sulfo-succinimidyl 4-(N-maleimidomethyl)cyclohexane-1-carboxylate (Sulfo-SMCC).

The maleimide chemical reaction group can easily form a covalent bond with a thiol group (—SH), so that a desired antibody, peptide, or the like can be easily introduced to the surface.

Figure 9:
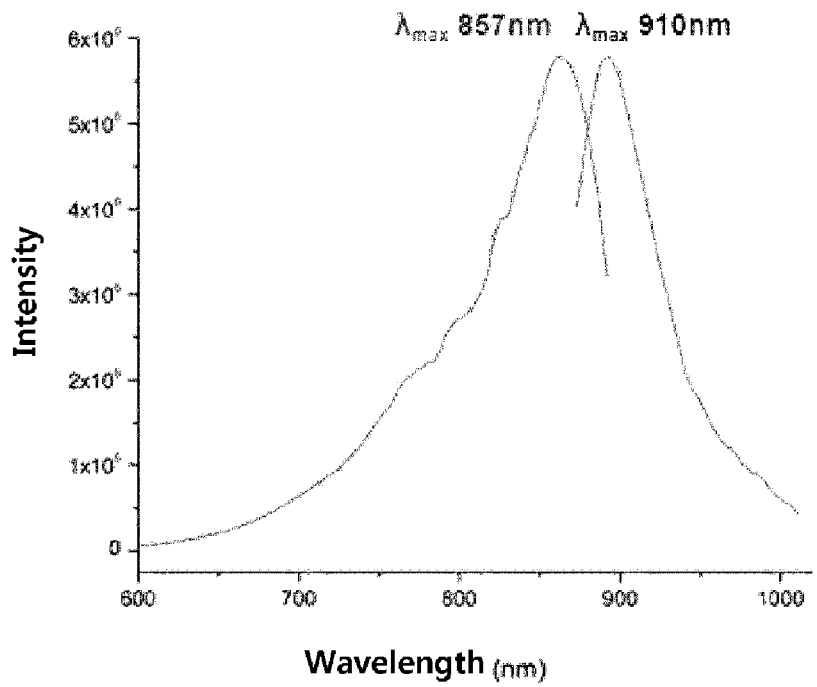
FIG. 9 shows an absorption wavelength and an emission wavelength of a nano near-infrared contrast medium prepared according to Preparation Example 1.

Then, in order to induce cancer cell-specific recognition and binding, a cancer cell-specific antibody was introduced to the maleimide chemical reaction group, thereby preparing a nano near-infrared contrast medium. The absorption wavelength and emission wavelength of the nano near-infrared contrast medium prepared according to the present preparation example are shown in FIG. 9.

Preparation Example 2

Contrast media were prepared by dissolving compound H per se according to Example 8 in various organic solvents without manufacturing core-shell nanoparticles.

Preparation Example 3

A contrast medium (DEX-dye) was prepared by introducing compound H according to Example 8 into a dextran polymer.

Preparation Example 4

A contrast medium (SiO$_2$NP-dye) was prepared by introducing Compound H according to Example 8 into SiO$_2$.

Test Example 1—Evaluation on Optical Properties of Contrast Medium According to Preparation Example 2

The absorption intensity, absorption wavelength, emission wavelength, and quantum yield (φf) of the contrast media prepared in Preparation Example 2 are shown in the Table 2.

TABLE 2

| Solvent | Absorption intensity (a.u) | Absorption wavelength (nm) | Emission wavelength (nm) | Φ$_f$ |
| --- | --- | --- | --- | --- |
| Acetone | 0.5 | 856 | 891 | 2.7 |
| CHCl$_3$ | 0.5 | 857 | 891 | 3.0 |
| DMF | 0.5 | 857 | 897 | 2.9 |
| EtOH | 0.5 | 857 | 890 | 3.1 |
| THF | 0.5 | 857 | 889 | 2.7 |
| DMSO | 0.51 | 857 | 877 | 3.2 |

As can be confirmed in Table 2 above, the compound according to the present invention has absorption wavelength and emission wavelength of long wavelength bands, and thus, can further increase the imaging depth and diagnose deep tissues (deep tissue imaging) when used as a contrast medium.

In addition, a conventional indocyanine green-based fluorescent contrast medium, which is currently applied to clinical practice, had a quantum efficiency (χf) of 2.58, but the compound according to the invention was analyzed to have superior optical properties by showing higher quantum efficiency than the conventional contrast medium.

Test Example 2—Evaluation on Optical Properties of Contrast Medium According to Preparation Example 1

The absorption intensity, absorption wavelength, emission wavelength, and quantum yield (φf) of the nano near-infrared contrast medium of Preparation Example 1 were measured, and the measurement results are shown in Table 3. As can be confirmed in Table 3 below, the contrast medium containing the core-shell nanoparticles had increased quantum efficiency compared with Preparation Example 2 without manufacturing nanoparticles.

TABLE 3

| Solvent | Absorption intensity (a.u) | Absorption wavelength (nm) | Emission wavelength (nm) | Φ$_f$ |
| --- | --- | --- | --- | --- |
| Deionized water | 0.49 | 850 | 900 | 3.5 |

Test Example 3—Evaluation on Light Safety of Nano Near-Infrared Contrast Media

Figure 10:
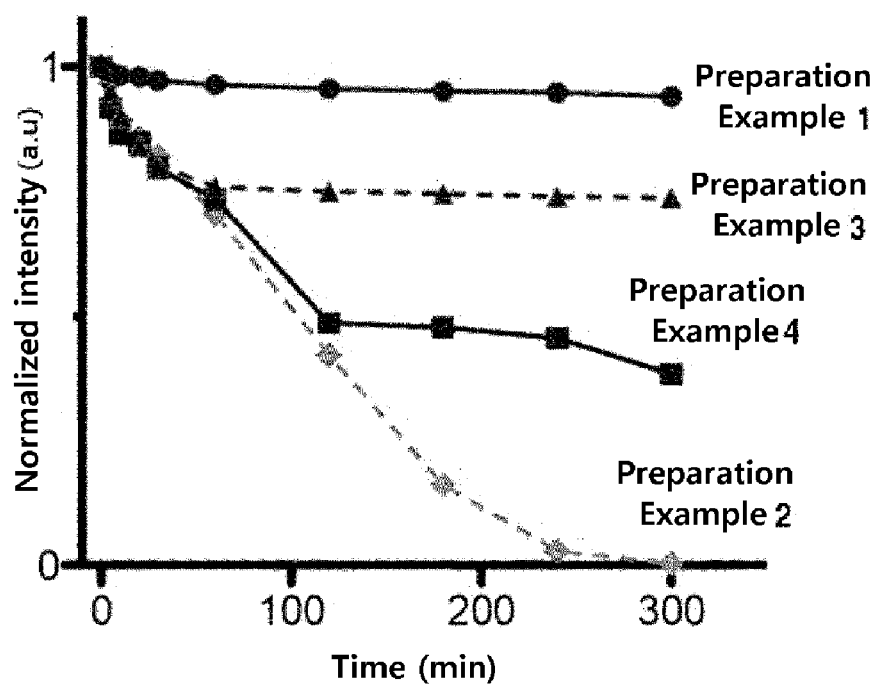
FIG. 10 shows the normalized intensity of the nano near-infrared contrast media prepared according to Preparation Examples 1 to 4.

The normalized intensity of the contrast media prepared in Preparation Examples 1 to 4 was determined. The normalized intensity refers to the intensity of the fluorescent substance emitted after the passage of time compared with the intensity of the fluorescent substance initially emitted under continuous light irradiation, and thus, the normalized intensity is a measure of the extent to which the light emission intensity is weakened. Test results could confirm that the photo-degradation phenomenon was more reduced (photo-bleaching was suppressed) in the contrast medium prepared in Preparation Example 1 rather than those in Preparation Examples 2 to 4 (see FIG. 10).

Figure 11:
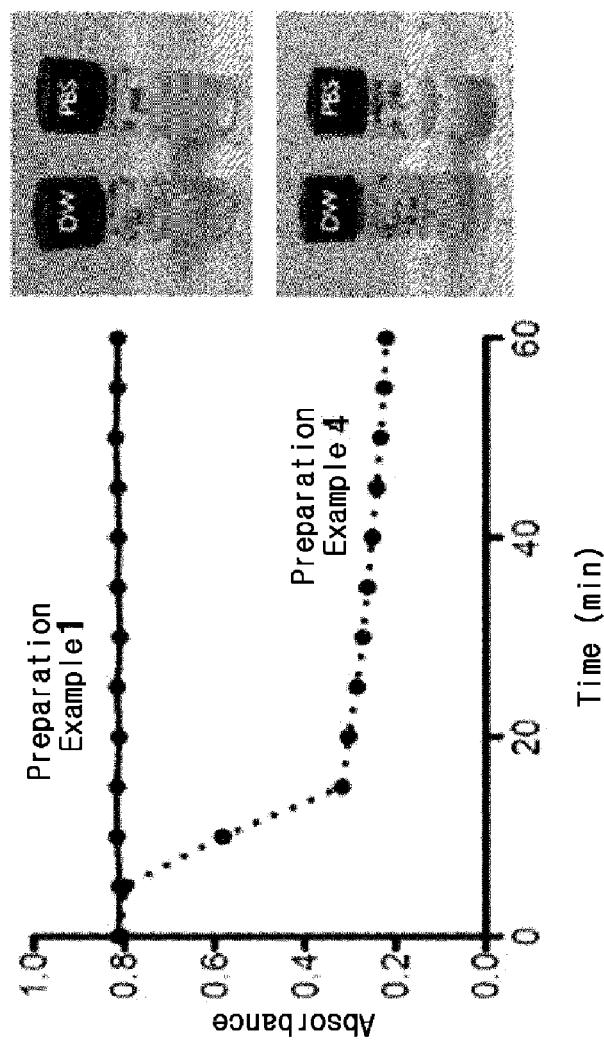
FIG. 11 shows the evaluation results on dispersibility in water of the nano near-infrared contrast media prepared according to Preparation Examples 1 to 4.

Test Example 4—Evaluation on Solvent Safety of Nano Near-Infrared Contrast Media As a result of evaluating the dispersibility of the nano near-infrared contrast media prepared in Preparation Examples 1 to 4 through UV-VIS spectrum analysis, the nano near-infrared contrast media were readily dispersed in water for a long time (see FIG. 11).

Test Example 5—Evaluation on Imaging Depth of Nano Near-Infrared Contrast Media

Figure 12:
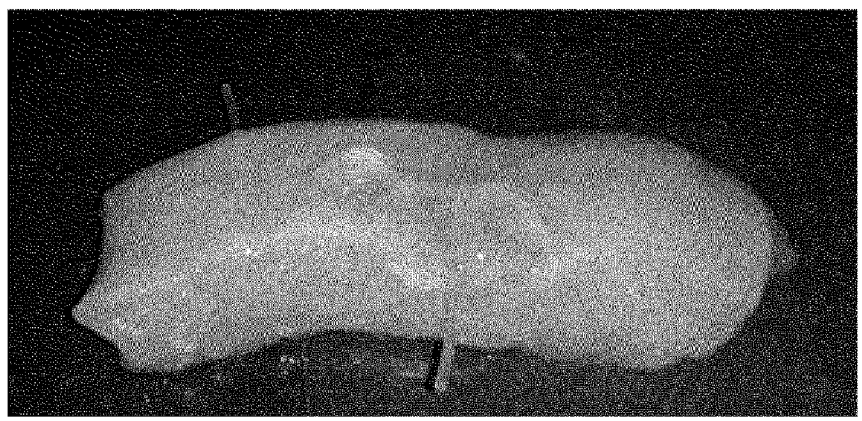
FIG. 12 shows an image of a chicken breast inserted with a tip of a near-infrared contrast medium prepared according to Preparation Example 1.
Figure 13:
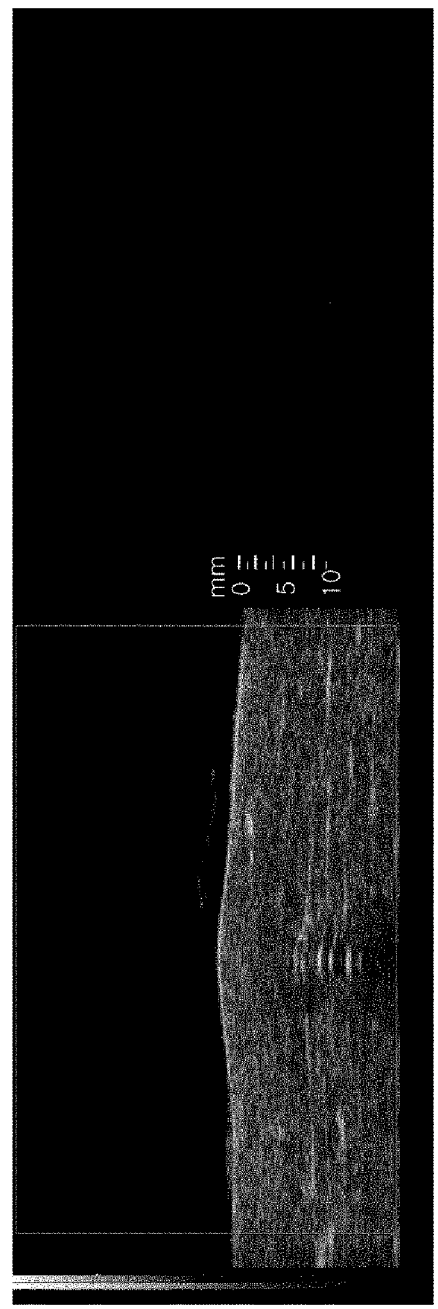
FIG. 13 shows the result of fluorescence analysis, using a photo-acoustic spectroscopy device, of the chicken breast inserted with a tip of a near-infrared contrast medium prepared according to Preparation Example 1.

A chicken breast inserted with a tip of a near-infrared contrast medium prepared according to Preparation Example 1 (see FIG. 12), and fluorescence analysis was carried out using a photo-acoustic spectroscopy device (Visualsonics, Vevo 3100 product). The results could confirm that the contrast ability (contrast at 10 mm or higher) of the contrast medium according to the present invention could be confirmed (see FIG. 13).

The invention claimed is:

1. A compound represented by Chemical Formula 1 or a salt thereof:

[Chemical Formula 1]

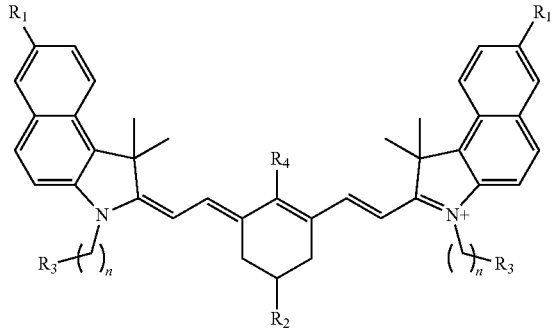

wherein,
$R_1$'s are each independently selected from —Br, —$SO_3H$, or OMe;
$R_2$ is —$CO_2H$, $C_1$-$C_3$ alkyl, $C_1$-$C_4$ alkylester,

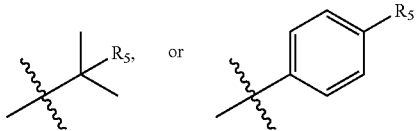

wherein $R_5$ is —H, —$CO_2H$, $C_1$-$C_3$ alkyl, or $C_1$-$C_4$ alkylester);
$R_3$ is -Me;
$R_4$ is —Cl or —S—$R_6$, wherein $R_6$ is

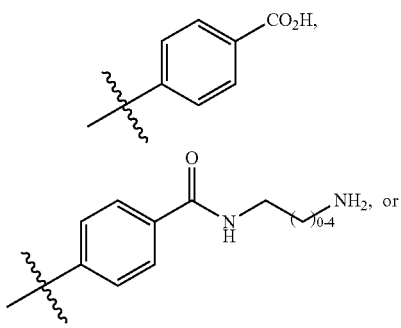

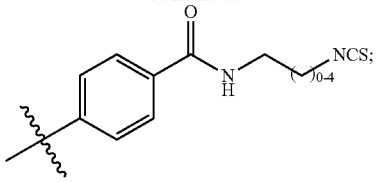

and n is 0-1.

2. The compound or salt thereof of claim 1, wherein $R_4$ is —S—$R_6$.

3. The compound or salt thereof of claim 2, wherein $R_2$ is

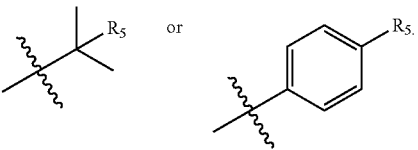

4. The compound or salt thereof of claim 1, wherein $R_4$ is —Cl.

5. The compound or salt thereof of claim 4, wherein $R_1$ is —OMe.

6. The compound or salt thereof of claim 4, wherein $R_2$ is

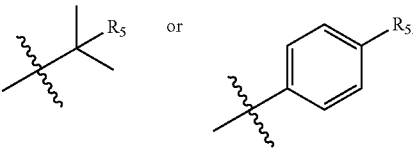

7. The compound or salt thereof of claim 1, wherein the compound of Chemical Formula 1 or salt thereof is selected from the group consisting of:
2-((E)-2-((E)-2-chloro-3-((E)-2-(3-ethyl-1,1-dimethyl-7-sulfo-1H-benzo[e]indo-1-2(3H)-ylidene)ethylidene)-5-(4-(methoxycarbonyl)phenyl)cyclohex-1-enyl)vinyl)-3-ethyl-1,1-dimethyl-1H-benzo[e]indolium-7-sulfonate;
7-bromo-2-((E)-2-((E)-3-((E)-2-(7-bromo-3-ethyl-1,1-dimethyl-1H-benzo[e]indol-2(3H)-ylidene)ethylidene)-2-chloro-5-(4-(methoxycarbonyl)phenyl)cyclohex-1-enyl)vinyl)-3-ethyl-1,1-dimethyl-1H-benzo[e]indolium iodide;
2-((E)-2-((E)-2-chloro-3-((E)-2-(3-ethyl-7-methoxy-1,1-dimethyl-1H-benzo[e]indol-2(3H)-ylidene)ethylidene)-5-(4-(methoxycarbonyl)phenyl)cyclohex-1-enyl)vinyl)-3-ethyl-7-methoxy-1,1-dimethyl-1H-benzo[e]indolium iodide;
2-((E)-2-((E)-2-chloro-3-((E)-2-(3-ethyl-1,1-dimethyl-7-sulfo-1H-benzo[e]indol-2(3H)-ylidene)ethylidene)-5-(1-methoxy-2-methyl-1-oxopropan-2-yl)cyclohex-1-enyl)vinyl)-3-ethyl-1,1-dimethyl-1H-benzo[e]indolium-7-sulfonate;
7-bromo-2-((E)-2-((E)-3-((E)-2-(7-bromo-3-ethyl-1,1-dimethyl-1H-benzo[e]indol-2(3H)-ylidene)ethylidene)-2-chloro-5-(1-methoxy-2-methyl-1-oxopropan-2-yl)cyclohex-1-enyl)vinyl)-3-ethyl-1,1-dimethyl-1H-benzo[e]indolium iodide;
2-((E)-2-((E)-2-chloro-3-((E)-2-(3-ethyl-7-methoxy-1,1-dimethyl-1H-benzo[e]indol-2(3H)-ylidene)ethylidene)-5-(1-methoxy-2-methyl-1-oxopropan-2-yl)cyclohex-1-enyl)vinyl)-3-ethyl-7-methoxy-1,1-dimethyl-1H-benzo[e]indolium iodide;

2-((E)-2-((E)-2-(4-carboxyphenylthio)-3-((E)-2-(3-ethyl-1,1-dimethyl-7-sulfo-1H-benzo[e]indol-2(3H)-ylidene)ethylidene)-5-(1-methoxy-2-methyl-1-oxopropan-2-yl)cyclohex-1-enyl)vinyl)-3-ethyl-1,1-dimethyl-1H-benzo[e]indolium-7-sulfonate;

4-((E)-6-((E)-2-(3-ethyl-7-methoxy-1,1-dimethyl-1H-benzo[e]indol-2(3H)-ylidene)ethylidene)-2-((E)-2-(3-ethyl-7-methoxy-1,1-dimethyl-1H-benzo[e]indolium-2-yl)vinyl)-4-(1-methoxy-2-methyl-1-oxopropan-2-yl)cyclohex-1-enylthio)benzoate;

2-((E)-2-((E)-2-(4-(2-aminoethylcarbamoyl)phenylthio)-3-((E)-2-(3-ethyl-7-methoxy-1,1-dimethyl-1H-benzo[e]indol-2(3H)-ylidene)ethylidene)cyclohex-1-enyl)vinyl)-3-ethyl-7-methoxy-1,1-dimethyl-1H-benzo[e]indolium iodide;

3-ethyl-2-((E)-2-((E)-3-((E)-2-(3-ethyl-7-methoxy-1,1-dimethyl-1H-benzo[e]indol-2(3H)-ylidene)ethylidene)-2-(4-(2-isothiocyantoethylcarbamoyl)phenylthio)-5-(1-methoxy-2-methyl-1-oxopropan-2-yl)cyclohex-1-enyl)vinyl)-7-methoxy-1,1-dimethyl-1H-benzo[e]indolium iodide;

2-((E)-2-((E)-2-(4-(2-aminoethylcarbamoyl)phenylthio)-3-((E)-2-(3-ethyl-7-methoxy-1,1-dimethyl-1H-benzo[e]indol-2(3H)-ylidene)ethylidene)cyclohex-1-enyl)vinyl)-3-ethyl-7-methoxy-1,1-dimethyl-1H-benzo[e]indolium iodide; and 2-((E)-2-((E)-2-(4-(2-aminoethylcarbamoyl)phenylthio)-5-tert-butyl-3-((E)-2-(3-ethyl-7-methoxy-1,1-dimethyl-1H-benzo[e]indol-2(3H)-ylidene)ethylidene)cyclohex-1-enyl)vinyl)-3-ethyl-7-methoxy-1,1-dimethyl-1H-benzo[e]indolium iodide.

8. A near-infrared fluorescent contrast medium containing, the compound of claim 1 or a pharmaceutically acceptable salt thereof.

9. The near-infrared fluorescent contrast medium of claim 8, wherein the contrast medium is a near-infrared fluorescent contrast medium for tumor imaging.

10. The near-infrared fluorescent contrast medium of claim 8, wherein the contrast medium is a near-infrared fluorescent contrast medium for angiography.

* * * * *

UNITED STATES PATENT AND TRADEMARK OFFICE
CERTIFICATE OF CORRECTION

| | |
|---|---|
| PATENT NO. | : 10,494,343 B2 |
| APPLICATION NO. | : 15/542454 |
| DATED | : December 3, 2019 |
| INVENTOR(S) | : Tae Jong Yoon et al. |

Page 1 of 1

It is certified that error appears in the above-identified patent and that said Letters Patent is hereby corrected as shown below:

On the Title Page

Item (54), "ORGANIC COMPOUND" should be --NOVEL ORGANIC COMPOUND--.

In the Specification

Column 1, Line 1, "ORGANIC COMPOUND" should be --NOVEL ORGANIC COMPOUND--.

Column 3, Line 3, "$R_5$" should be --$R_6$--.

Column 4, Line 34, "$R_5$" should be --$R_6$--.

Column 21, Line 52, "Formula or" should be --Formula 1 or--.

Signed and Sealed this
Twenty-first Day of January, 2020

Andrei Iancu
*Director of the United States Patent and Trademark Office*